US 11,413,397 B2

(12) United States Patent
Karp et al.

(10) Patent No.: US 11,413,397 B2
(45) Date of Patent: Aug. 16, 2022

(54) SYSTEM AND METHOD FOR RESISTANCE-DEPENDENT, SELF-REGULATED MEDICAL PENETRATION

(71) Applicant: THE BRIGHAM AND WOMEN'S HOSPITAL, INC., Boston, MA (US)

(72) Inventors: Jeffrey Karp, Brookline, MA (US); Girish Chitnis, Newton, MA (US); Julien Lamazouade, Arsac (FR); Mohan K. S. Verma, Agra (IN)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 599 days.

(21) Appl. No.: 16/469,567

(22) PCT Filed: Dec. 15, 2017

(86) PCT No.: PCT/US2017/066597
§ 371 (c)(1),
(2) Date: Jun. 13, 2019

(87) PCT Pub. No.: WO2018/112305
PCT Pub. Date: Jun. 21, 2018

(65) Prior Publication Data
US 2020/0069883 A1 Mar. 5, 2020

Related U.S. Application Data

(60) Provisional application No. 62/435,494, filed on Dec. 16, 2016.

(51) Int. Cl.
A61M 5/315 (2006.01)
A61M 5/20 (2006.01)
A61M 5/31 (2006.01)

(52) U.S. Cl.
CPC . *A61M 5/31573* (2013.01); *A61M 2005/2026* (2013.01); *A61M 2005/3132* (2013.01)

(58) Field of Classification Search
CPC .. A61M 5/46; A61M 5/31573; A61M 5/2033; A61M 5/31566; A61M 5/31571;
(Continued)

(56) References Cited

U.S. PATENT DOCUMENTS 3,923,058 A 12/1975 Weingarten
4,064,879 A 12/1977 Leibinsohn
(Continued)

FOREIGN PATENT DOCUMENTS

EP 2380622 A1 10/2011
JP 4505561 B1 7/2010
(Continued)

OTHER PUBLICATIONS

International Search Report and Written Opinion for International Application PCT/US2017/066597, dated Mar. 8, 2018, 10 pages.
(Continued)

*Primary Examiner* — Tiffany Legette
(74) *Attorney, Agent, or Firm* — Quarles & Brady LLP

(57) ABSTRACT

A system for delivering an injection of a fluid into a void within a subject is disclosed. A barrel extends from a first end to a second end and forms a lumen extending from the first end to the second end. A plug and a floating seal are arranged within the lumen. A hollow needle includes a distal end with an opening for fluid to flow from the lumen. The plug, the barrel and the floating seal include material and dimensions selected based on a threshold flowrate for a fluid arranged within the lumen to: overcome a force opposed to a force being applied to the fluid in the lumen to move the floating seal and the hollow needle into a tissue of the
(Continued)

subject, and succumb to the opposing force to displace the fluid through the opening into the void.

20 Claims, 37 Drawing Sheets

(58) Field of Classification Search
CPC ...... A61M 5/328; A61M 5/286; A61M 5/284;
A61M 5/315667; A61M 2005/2026;
A61M 2005/2073; A61M 2005/208;
A61M 2005/3132; A61M 2005/1787;
A61B 117/3401

See application file for complete search history.

(56) References Cited

U.S. PATENT DOCUMENTS

| | | | |
|---|---|---|---|
| 4,067,333 A | 1/1978 | Reinhardt et al. | |
| 4,275,730 A | 6/1981 | Hussein | |
| 4,394,863 A | 7/1983 | Bartner | |
| 4,624,659 A | 11/1986 | Goldberg et al. | |
| 4,869,717 A | 9/1989 | Adair | |
| 5,215,523 A | 6/1993 | Williams et al. | |
| 5,270,685 A | 12/1993 | Hagen et al. | |
| 5,722,955 A | 3/1998 | Racz | |
| 5,902,273 A | 5/1999 | Yang et al. | |
| 6,719,736 B2 | 4/2004 | Collins et al. | |
| 7,351,223 B2 | 4/2008 | Call | |
| 8,197,435 B2 | 6/2012 | Prausnitz et al. | |
| 8,291,768 B2 | 10/2012 | Spiegel et al. | |
| 8,419,764 B2 | 4/2013 | Begg | |
| 8,636,713 B2 | 1/2014 | Prausnitz et al. | |
| 8,920,388 B2 | 12/2014 | Slocum et al. | |
| 2002/0035351 A1* | 3/2002 | Lodice | A61M 5/284 604/221 |
| 2003/0199846 A1 | 10/2003 | Ramming | |
| 2004/0171984 A1 | 9/2004 | Greenfield | |
| 2007/0100288 A1 | 5/2007 | Bozeman et al. | |
| 2009/0318864 A1 | 12/2009 | Carrel et al. | |
| 2012/0095409 A1 | 4/2012 | Lanin | |
| 2012/0271272 A1 | 10/2012 | Hammack et al. | |
| 2013/0216623 A1 | 8/2013 | Yamamoto et al. | |
| 2015/0051581 A1 | 2/2015 | Andino et al. | |

FOREIGN PATENT DOCUMENTS

| | | |
|---|---|---|
| WO | 2009023247 A1 | 2/2009 |
| WO | 2013022604 A1 | 2/2013 |
| WO | 2013191394 A1 | 12/2013 |
| WO | 2014028285 A1 | 2/2014 |
| WO | 2014074823 A1 | 5/2014 |

OTHER PUBLICATIONS

European Patent Office, Extended European Search Report for application 17880420.9. dated May 27, 2020.

* cited by examiner

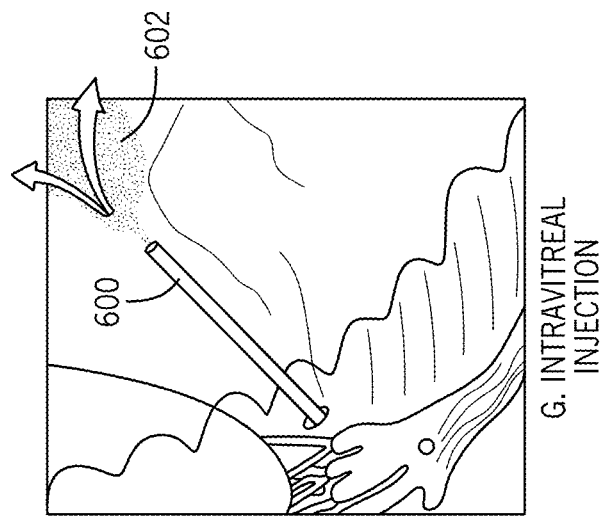
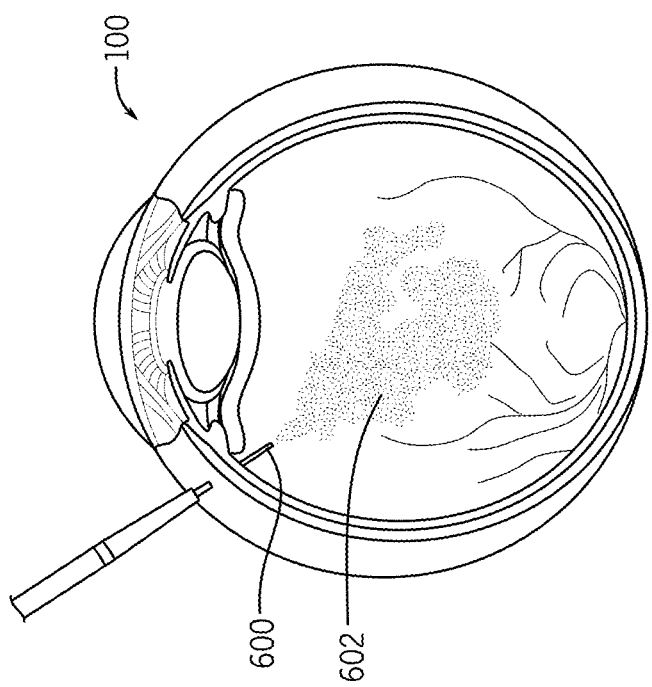
FIG. 6B
FIG. 6A

SYSTEM AND METHOD FOR RESISTANCE-DEPENDENT, SELF-REGULATED MEDICAL PENETRATION

CROSS-REFERENCE TO RELATED APPLICATIONS

This application represents the national stage entry of international application PCT/US2017/066597, filed Dec. 15, 2017, which claims benefit of U.S. Provisional Application 62/435,494 filed Dec. 16, 2016. All of which are incorporated herein by reference for all purposes.

BACKGROUND

The present disclosure relates to systems and methods for penetration devices used in medical applications. More particularly, the present disclosure provides systems and methods to improve the positional accuracy of penetration devices and, specifically, penetration devices relating to cavities.

Penetration devices such as needles are often used to inject or drain cavities. Issues arise when the individual using the needle is unable to confirm the needle's entrance into a cavity. This type of blind insertion can result in a procedure that is only partially successful, or even a failed procedure.

Current cavity sensing needles are only useful in certain procedures, as they are typically one size per needle. Current solutions also lack the sensitivity necessary for substantially small cavities. One example of such a cavity is the suprachoroidal space, located between the sclera and the choroid within the eye.

The suprachoroidal space has been explored as a potential site for drug delivery to target the back of the eye. This region of the eye, called the posterior segment, has several associated diseases that benefit from drug treatment. Drug delivery via the suprachoroidal space has been shown to be more effective than direct intravitreal injections to the posterior segment. However, determining needle entrance to the suprachoroidal space is both critical to the success of the drug treatment, as well as very difficult to achieve.

Current cavity sensing needles are too large for optical use, and lack the sensitivity necessary to detect the suprachoroidal space.

A system and method for a penetration device that has improved sensitivity and positional accuracy is therefore desired.

SUMMARY

The present disclosure provide a penetration device that employs a new self-regulatory design, via resistance, to achieve accurate penetration device placement. The new penetration device can be particularly accurate when employed relative to a cavity, and can achieve higher performance than conventional penetration devices and methods.

In accordance with one aspect of the present disclosure, a system for delivering an injection of a fluid to a void within a subject is described. The system includes a syringe barrel extending from a first end to a second end and forming a lumen extending from the first end to the second end. The system further includes a plug arranged within the lumen proximate to the first end. The plug forms a seal between the plug and the syringe barrel against fluid movement from the lumen between the plug and the syringe barrel. The system additionally includes a floating seal arranged within the lumen proximate to the second end forming a seal between the floating seal and the syringe barrel against fluid movement from the lumen between the floating seal and the syringe barrel. The system further includes a hollow needle extending from a proximal end connected to the floating seal to a distal end having an opening formed at the distal end for fluid to flow from the lumen, through the floating seal, and through the second end of the syringe barrel via the hollow needle. The syringe barrel, the plug, and the floating seal include material and dimensions selected based on a threshold flowrate for a fluid arranged within the lumen. The threshold flowrate of the fluid is used to, upon applying a force or pressure to the fluid, overcome an opposing force so that the floating seal and hollow needle move from the second end of the syringe barrel and the distal end of the hollow needle extends into a tissue of the subject. The threshold flowrate of the fluid is further used to, upon the distal end of the hollow needle extending beyond the tissue of the subject and into a void, succumb to the opposing force to displace the fluid through the opening formed at the distal end of the hollow needle into the void.

In accordance with one aspect of the present disclosure, a method for delivering an injection of a fluid to a void within a subject is described. The method includes providing a syringe system including: a syringe barrel extending from a first end to a second end and forming a lumen extending from the first end to the second end, a plug arranged within the lumen proximate to the first end and forming a seal between the plug and the syringe barrel against fluid movement from the lumen between the plug and the syringe barrel, a floating seal arranged within the lumen proximate to the second end forming a seal between the floating seal and the syringe barrel against fluid movement from the lumen between the floating seal and the syringe barrel, and a hollow needle extending from a proximal end connected to the floating seal to a distal end having an opening formed at the distal end for fluid to flow from the lumen, through the floating seal, and through the second end of the syringe barrel via the hollow needle. The method further includes arranging the distal end of the hollow needle to extend into the tissue without applying a force to the fluid. The method additionally includes applying a force to the fluid to overcome an opposing force to move the floating seal and hollow needle from the second end of the syringe barrel and extend the distal end of the hollow needle further into the tissue of the subject. The method further includes continuing said applying the force to the fluid as the distal end of the hollow needle extends beyond the tissue of the subject and into the void as the floating seal succumbs to the opposing force between the floating seal and the syringe barrel to displace the fluid through the opening formed at the distal end of the hollow needle into the void.

The foregoing and other advantages of the present disclosure will appear from the following description. In the description, reference is made to the accompanying drawings, which form a part hereof, and in which there is shown by way of illustration a preferred embodiment of the disclosure. Such embodiment does not necessarily represent the full scope of the disclosure, however, and reference is made therefore to the claims and herein for interpreting the scope of the disclosure.

BRIEF DESCRIPTION OF THE DRAWINGS

FIG. 6A shows an intravitreal injection to the posterior eye segment in accordance with the present disclosure.

FIG. 6B shows a second view of the intravitreal injection of FIG. 6A in accordance with the present disclosure.

DETAILED DESCRIPTION

Figure 1A:
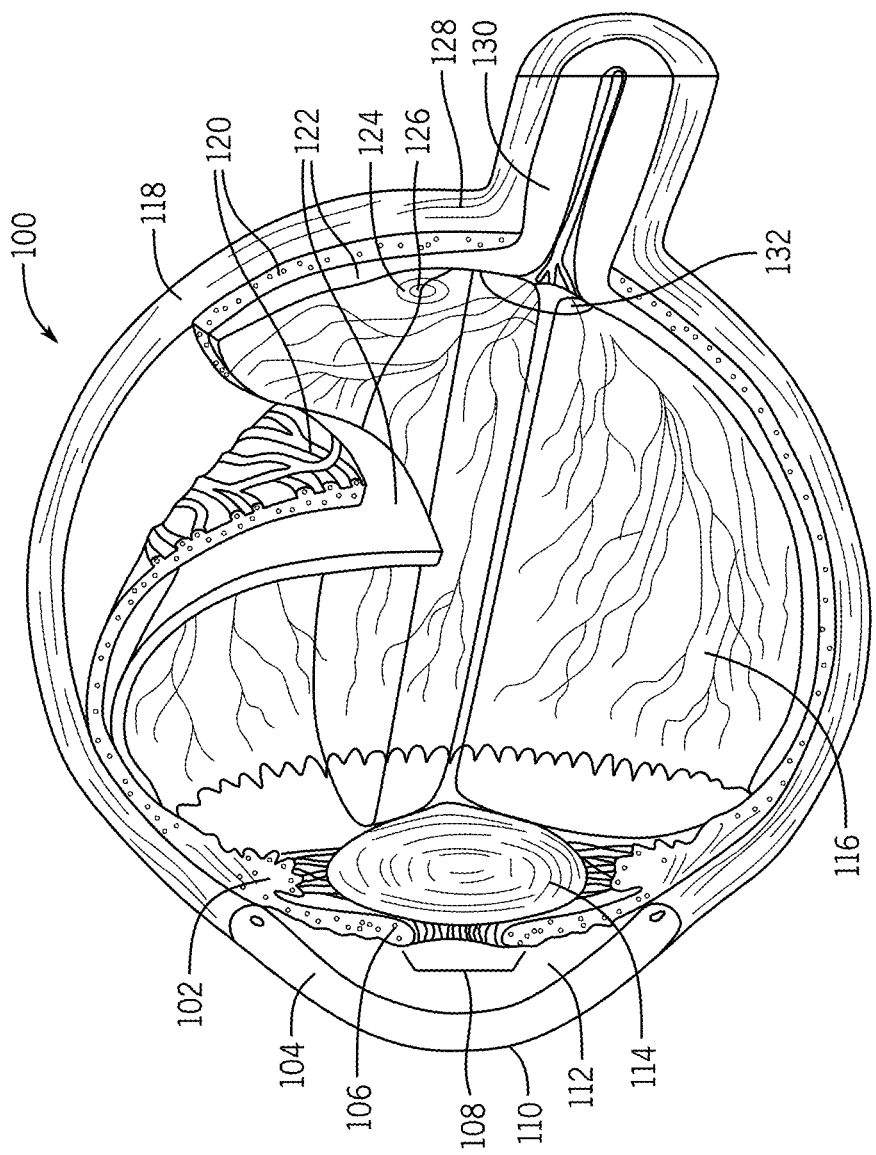
FIG. 1A shows the anatomy of an eye in accordance with the present disclosure.
Figure 1B:
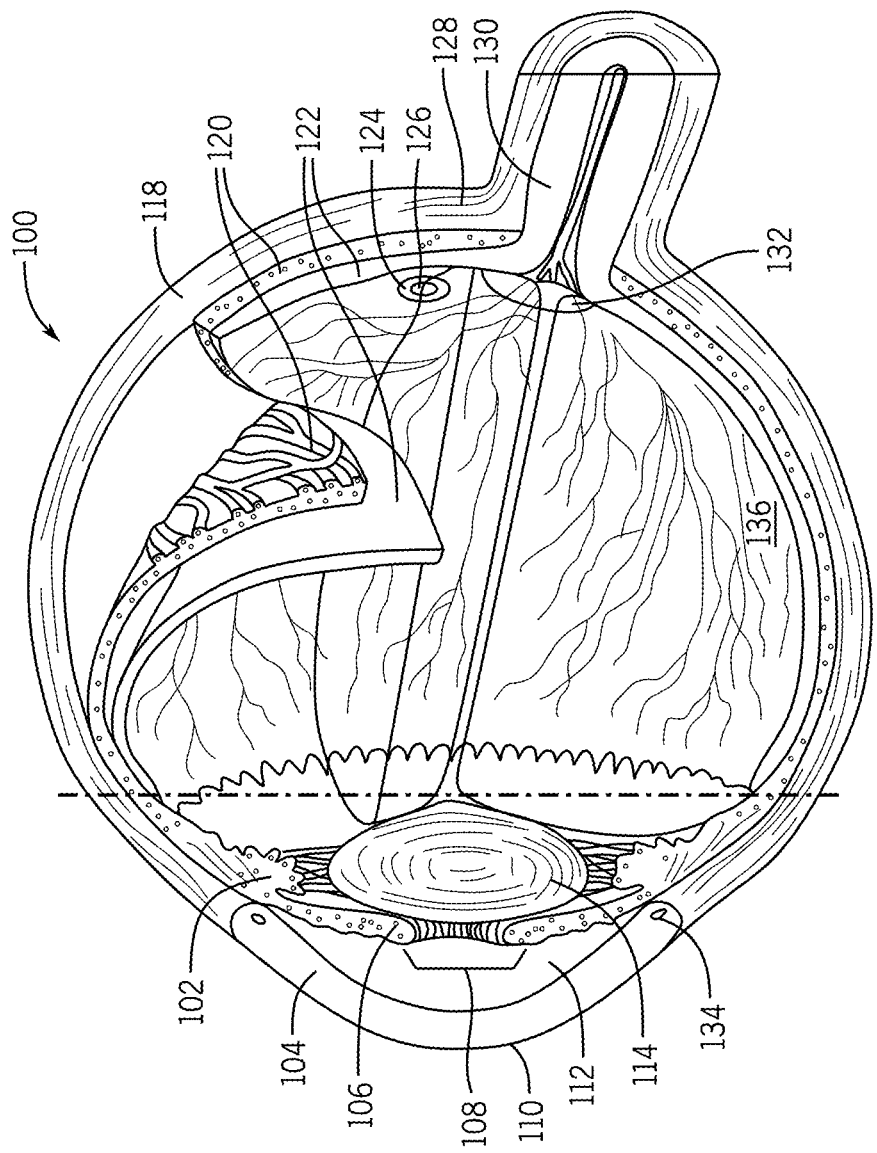
FIG. 1B shows the eye segments of FIG. 1A in accordance with the present disclosure.

FIG. 1A shows the basic anatomy of an eye 100. The eye 100 includes: the ciliary body 102, the cornea 104, the iris 106, the pupil 108, the anterior pole 110, the anterior segment 112, the lens 114, the posterior segment 116, the sclera 118, the choroid 120, the retina 122, the macula lutea 124, the fovea centralis 126, the posterior pole 128, the optic nerve 130, and the optic disc 132. As shown by FIG. 1B, the eye 100 can be defined by two distinct segments, the anterior segment 134 and the posterior segment 136. The posterior segment 136 can be affected by a multitude of eye diseases including macular degeneration (AMD), diabetic retinopathy (DR), diabetic macular edema (DME), retinal vein occlusion (RVO), uveitis, and endophthalmitis. These eye diseases are a major cause of permanent visual impairment, and affect millions of people.

Figure 2:
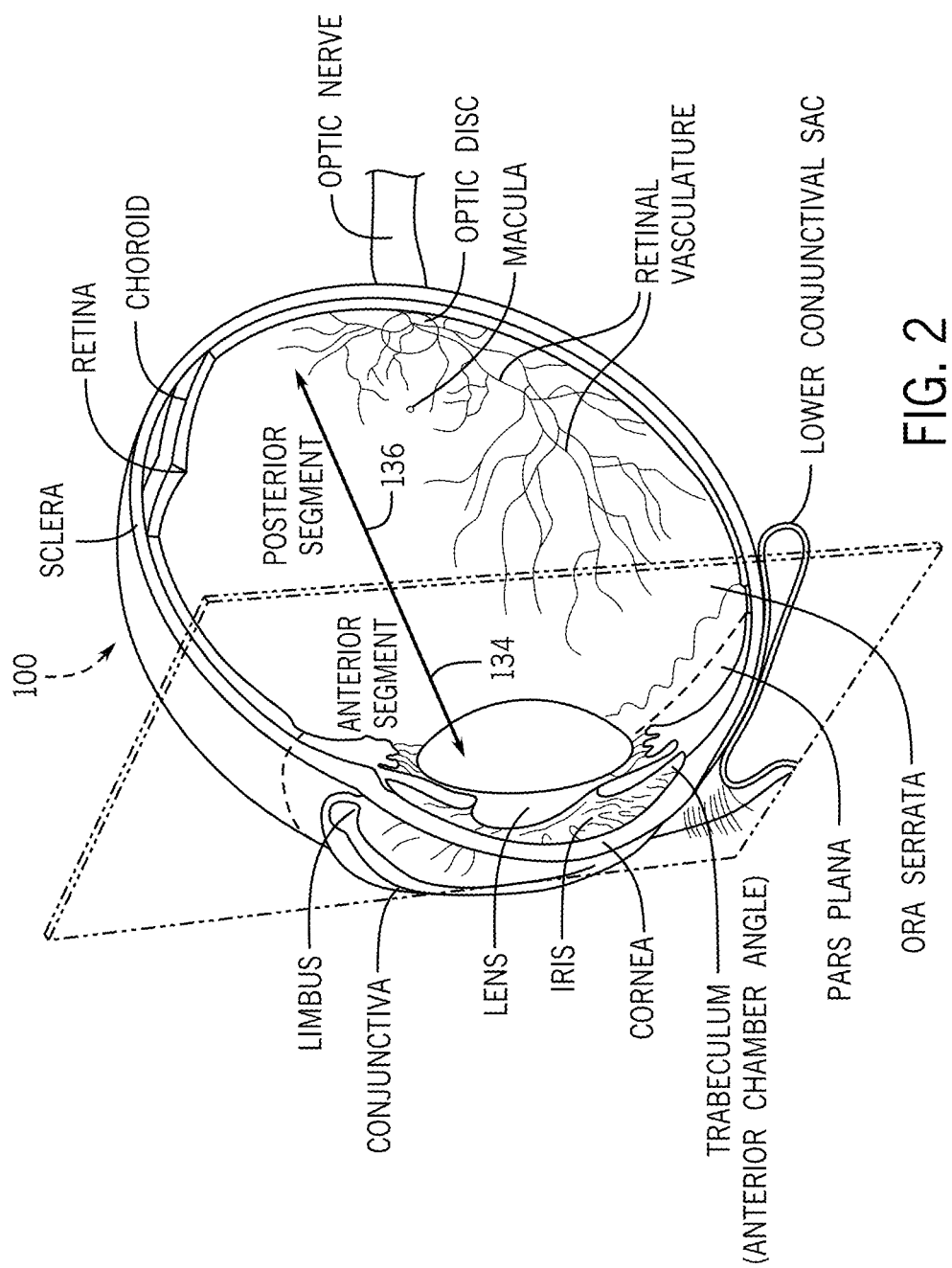
FIG. 2 shows the anatomy of an eye as it relates to posterior segment eye (PSE) diseases in accordance with the present disclosure.

FIG. 2 shows the eye 100 by the anterior segment 134 and the posterior segment 136, as well as the terminology specific to the eye diseases that affect the posterior segment 136.

Figure 3:
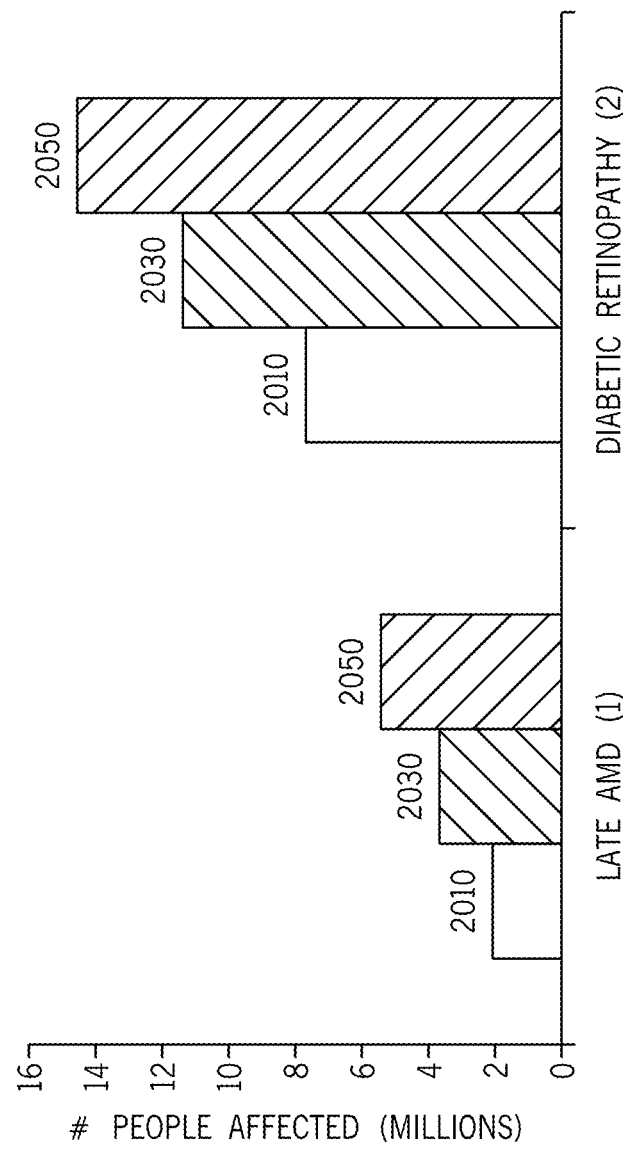
FIG. 3 is a graph depicting the prevalence of PSE diseases over time in accordance with the present disclosure.

FIG. 3 is a graphical representation of the increasing prevalence of posterior segment 136 eye diseases. As shown, the National Eye Institute predicts a steady upward trend from 2010 to 2050 for both late AMD and diabetic retinopathy. As the prevalence of these diseases increases, it becomes even more critical to find a successful method for drug delivery.

Figure 4B:
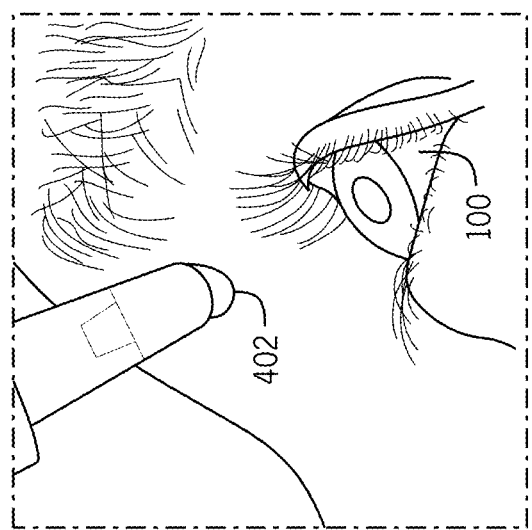
FIG. 4B shows another treatment option for PSE diseases.
Figure 4A:
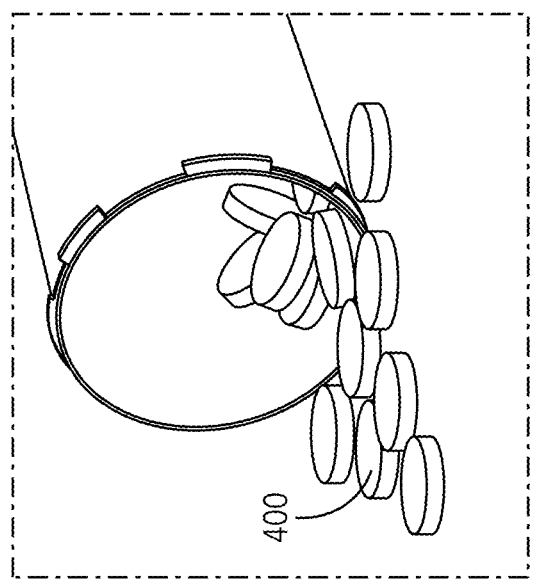
FIG. 4A shows a t treatment option for PSE diseases.

FIG. 4A shows one method of treatment, orally administered drug 400. Orally administered drug 400 does not provide sufficient treatment for posterior segment diseases, because there can be limitations of systemic delivery due to the blood-eye barrier. In many cases, the necessary therapeutic level of the drug cannot be achieved via orally administered drug 400. In addition, orally administered drug 400 can lead to unwanted side-effects due to systemic availability.

FIG. 4B shows another method of treatment, ocular administered drug 402. However, localized delivery to the eye 100 through topical application is also limited when trying to reach the effective drug amount.

Figure 5:
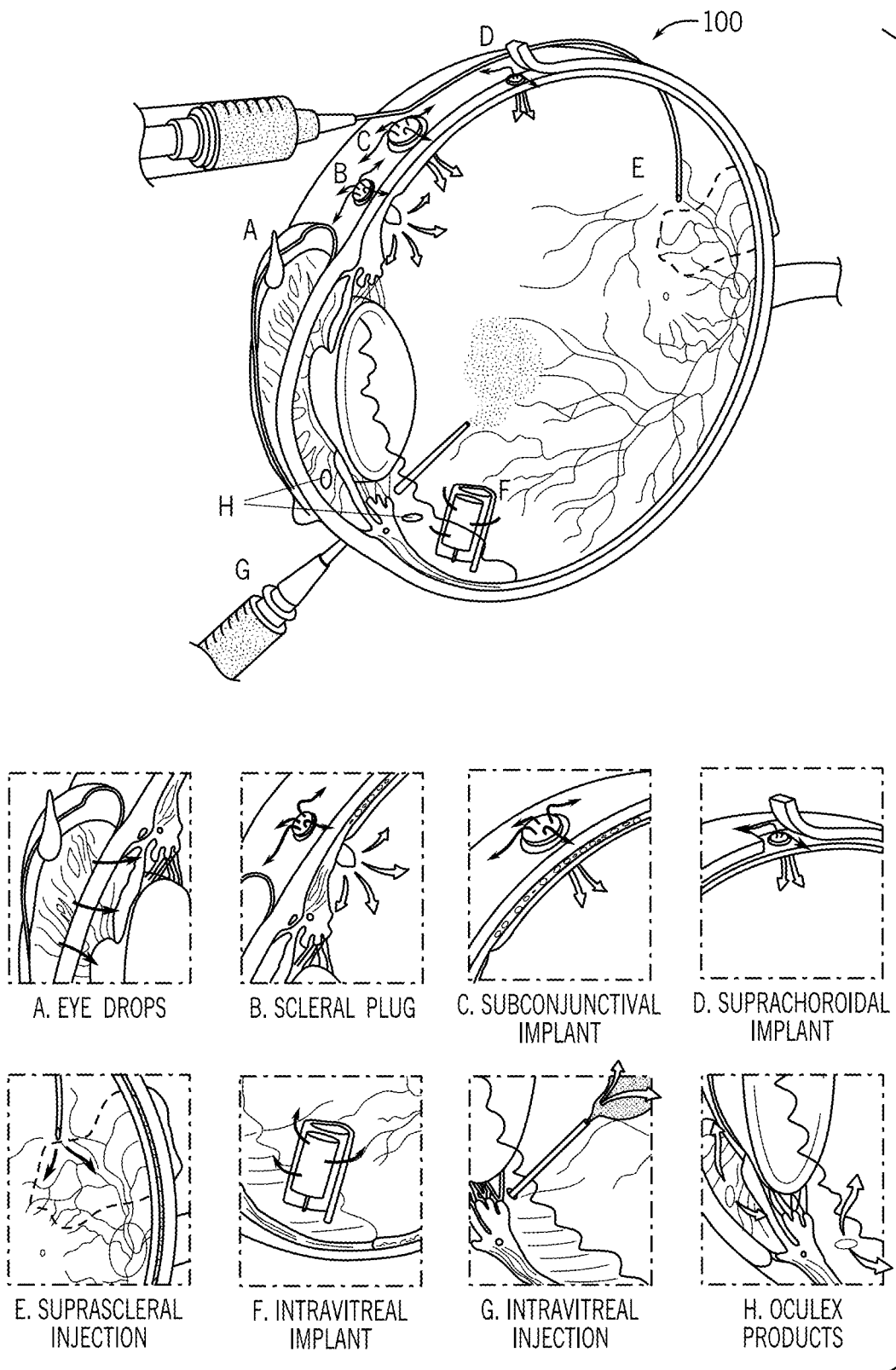
FIG. 5 shows drug delivery routes for the posterior eye segment.

FIG. 5 depicts drug delivery routes for the posterior segment 116 of eye 100. Eye drops, a scleral plug, a subconjunctival implant, a suprachoroidal implant, a suprachoroid injection, an intravitreal implant, an intravitreal injection, and oculex products are all current methods directed to delivering treatment to eye 100.

FIGS. 6A and 6B show a method for delivering treatment to eye 100, intravitreal injection 600. Here, an intravitreal injection 600 facilitates the delivery of intravitreal drug 602 to the eye 100. Although the incidence is low, there can be serious complication associated with the intravitreal injection 600, including retinal detachment, cataract, and hemorrhage. These complications can result due to the inherently more invasive nature of the treatment. In addition to the possibility of serious complications, the intravitreal injection 600 has other major drawbacks. Intravitreal injection 600 has poor dosage control, as the intravitreal drug 602 has limited exposure to the retina 122. Additionally, there is no way to significantly select the posterior segment 136 over the anterior segment 134. Further, the intravitreal injection 600 can require multiple clinic visits for multiple injections.

Figure 7:
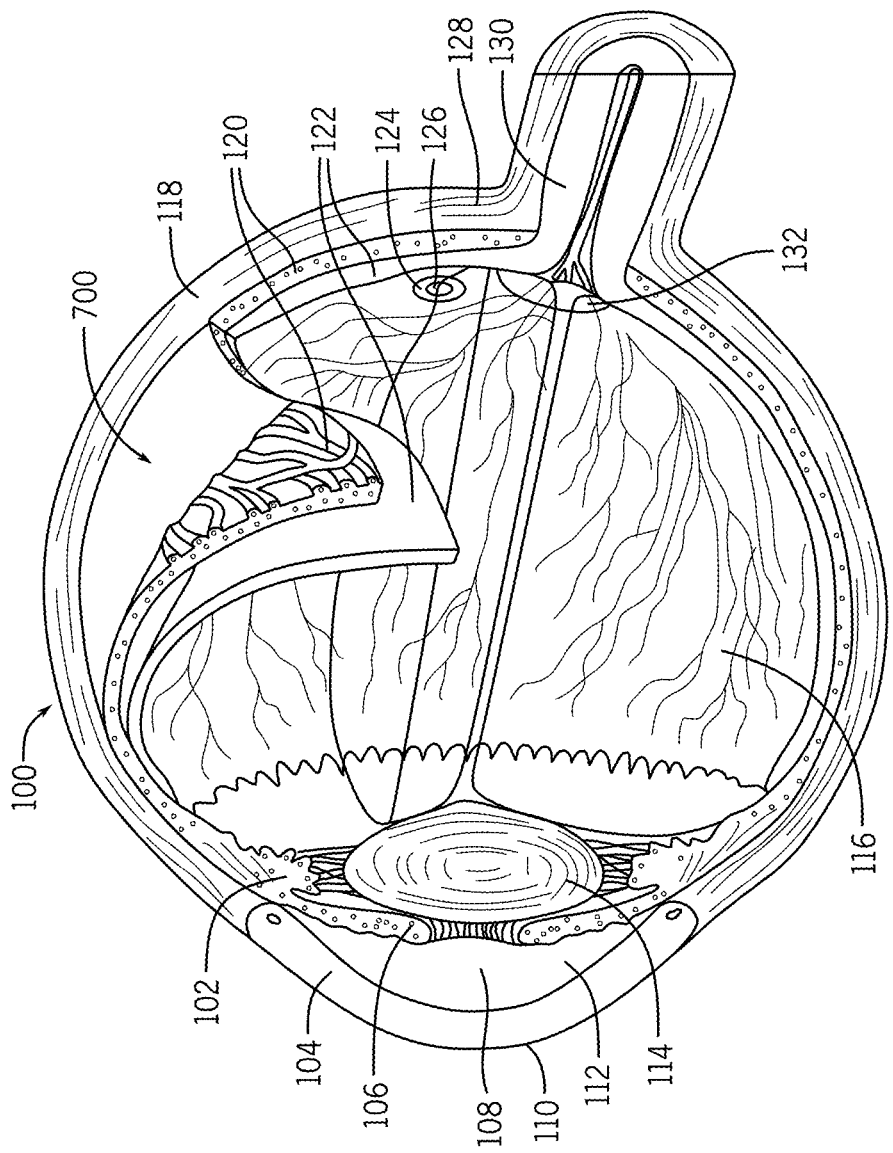
FIG. 7 shows the anatomy of an eye as it relates to the suprachoroidal space (SCS) in accordance with the present disclosure.

FIG. 7 shows a newer treatment option, where a drug is administered via the suprachoroidal space (SCS) 700, which is the cavity located between the sclera 118 and the choroid 120.

Figure 8A:
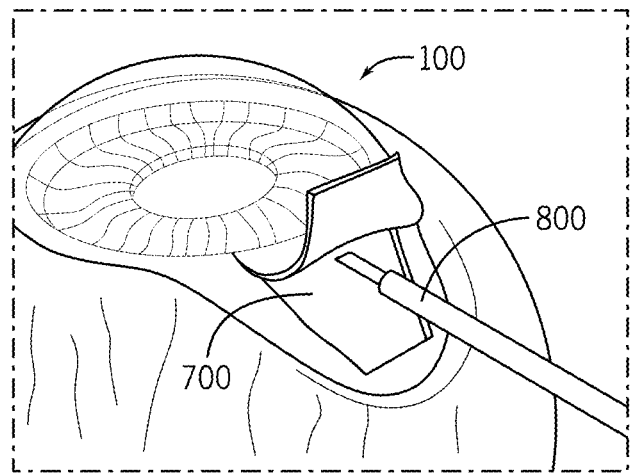
FIG. 8A shows one method for reaching the SCS.

FIG. 8A shows a method for treatment via suprachoroidal space 700. An incision is created in the eye 100 by instrument 800. This method enables a controlled and targeted delivery of drugs by using a micro-catheter, but is an invasive procedure.

Figure 8B:
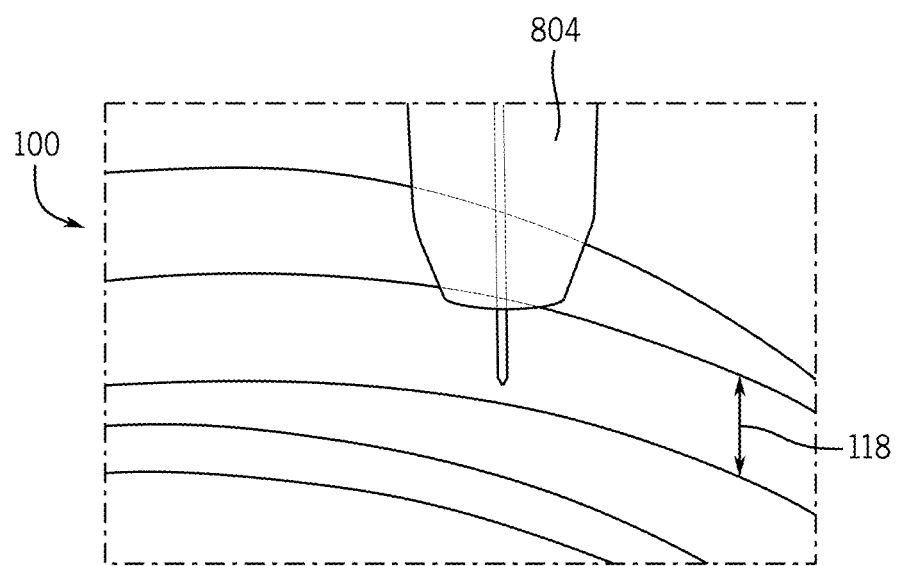
FIG. 8B shows another method for reaching the SCS.

FIG. 8B shows another method for treatment via the suprachoroidal space 700. A hollow microneedle 804 is used to provide treatment to the eye 100. The hollow microneedle 804 has a predefined length that limits needle penetration to a predetermined depth into the sclera 118. This method allows for controlled and targeted delivery, and is also minimally invasive. However, the sclera depth varies significantly from patient to patient, and therefore mapping of eye geometry would be necessary prior to the insertion of the hollow microneedle 804 to successfully target the suprachoroidal space 700.

As will be described, a self-regulating or "autostop" penetration system in accordance with the present disclosure may be designed for use in a variety of applications, including, as a non-limiting example, to deliver or drain fluid from the suprachoroidal space 700. As will be described, the self-regulating penetration system may be used with any application that involves reaching a void or cavity, for example, a cavity that is not visually apparent to the user of the self-regulating penetration system.

Figure 9:
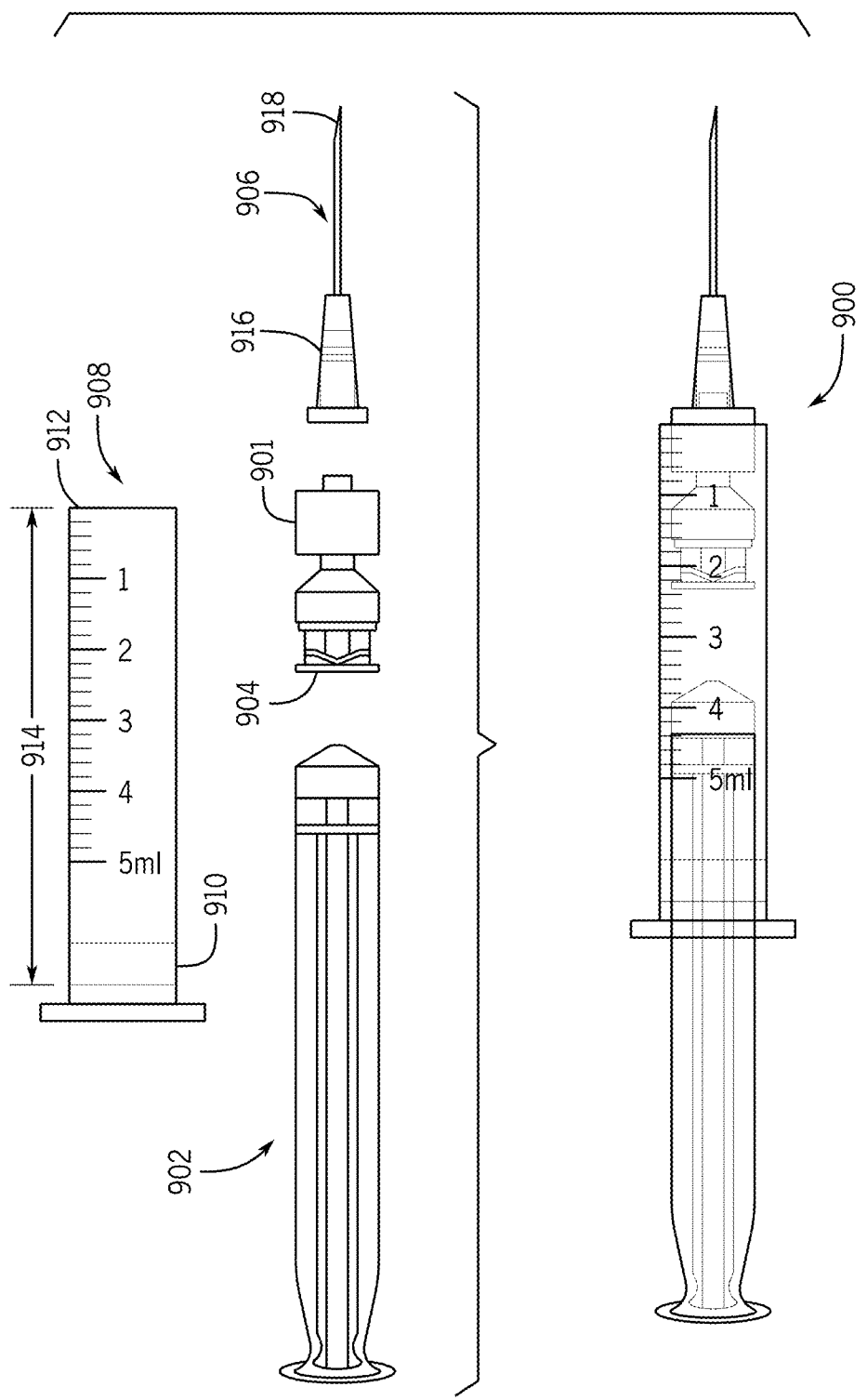
FIG. 9 shows an autostop needle in accordance with the present disclosure.

Referring to FIG. 9, one example of a self-regulating penetration system is illustrated, which is shown in the form of an autostop syringe or needle 900. The autostop needle 900 may include a plug 901, a plunger 902, a seal 904, a penetrating device or needle 906, and a barrel 908. Penetrating device 906 is illustrated as a needle, but the device 906 may take the form of other penetrating devices that are designed to extend through tissue, such as drills, spears, boring devices, and the like. The barrel extends from a first end 910 to a second end 912 and forms a lumen 914 extending therebetween. The plug 901 is designed to have a frictional coupling to the interior of the barrel 908, creating a seal at the second end 912 of the lumen 914.

Compared to a standard syringe, the autostop needle 900 includes the seal 904 that floats, allowing the needle 906 to move within the lumen 914 independent of the barrel 908. To this end, the seal 904 may be referred to as a floating seal. The needle 906 may be hollow. The hollow needle 906 extends from a proximal end 916 connected to the floating seal 904 to a distal end 918 having an opening formed at the distal end 918 to provide a passage for fluid to flow from the lumen 914, through the floating seal 904, and through the second end 912 of the syringe barrel 908 via the hollow needle 906. The fluid may include a liquid, a gas, a combination of liquid and gas, liquid-suspended particles, gel, gel-suspended particles, micro-particles, nano-particles, shear-thinning substances (i.e., solids that become a fluid when exposed to shearing forces, such as can be presented when press on the needle) and the like. The fluid may be a therapeutic agent. For example, in the non-limiting example of delivering a therapeutic agent to an eye, the therapeutic agent may include, as non-limiting examples, adalimumab, Humira (adalimumab), Jetrea (ocriplasmin), Lucentis (ranibizumab injection), Zioptan (tafluprost ophthalmic solution), Eylea (aflibercept), Zymaxid (gatifloxacin ophthalmic solution), Acuvail (ketorolac tromethamine), Ozurdex (dexamethasone), Macugen (pegaptanib), Lumigan (bimatoprost ophthalmic solution), Travatan (travoprost ophthalmic solution), Valcyte (valganciclovir HCl), Betaxon, Visudyne (verteporfin for injection), Alphagan (brimonidine), Vistide (cidofovir), and the like.

Figure 10:
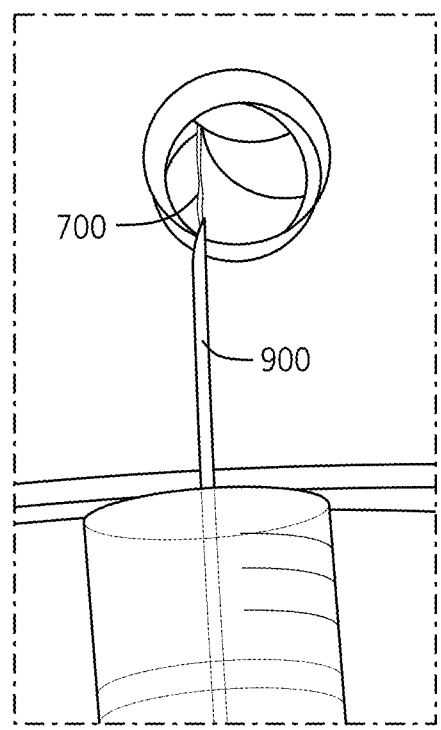
FIG. 10 shows an autostop needle within the SCS in accordance with the present disclosure.

The material selection and dimensions of the syringe barrel 908, the plug 901, and the floating seal 904 are selected based on a threshold flowrate for a fluid arranged within the lumen 914 to achieve a self-regulating or autostop function. That is, as will be further detailed, in operation, the tip of the needle 906 may be inserted a minimal depth into tissue to present a resistance to fluid flow from the barrel 908 through the needle 906. As will be described, an opposing force (e.g., the frictional force of the floating seal 904) is designed to restrict backward motion during the pre-insertion to a void or cavity. However, as will be described, when the needle 906 reaches a void or cavity, further penetration is restricted and fluid flow through the needle 906 is permitted. As one non-limiting example, FIG. 10 shows the autostop needle 900 once it has entered the suprachoroidal space 700.

Figure 11A:
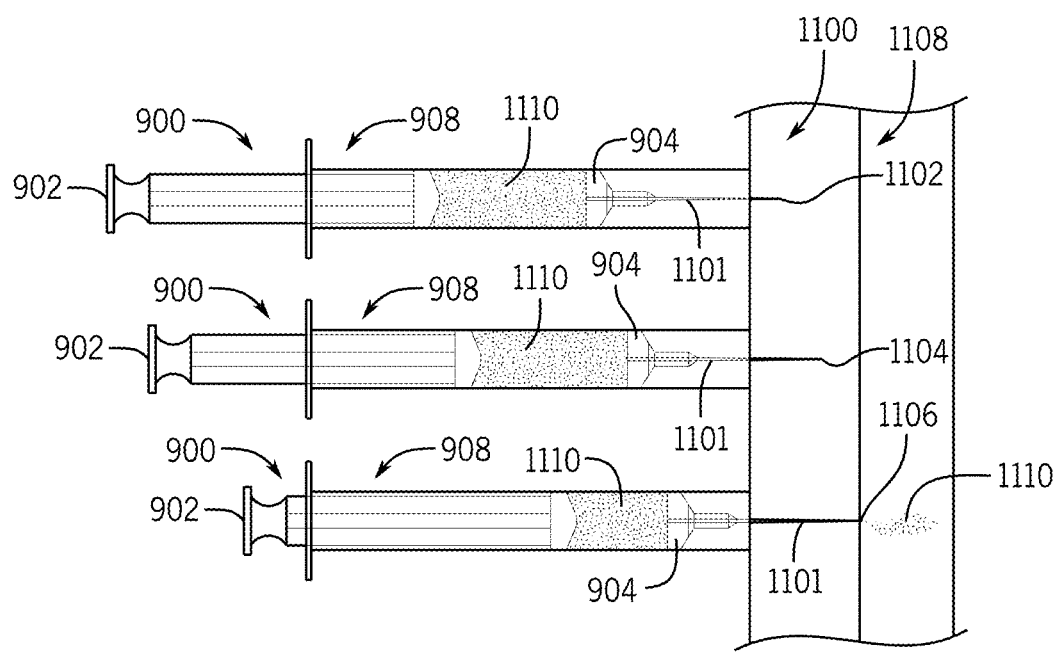
FIG. 11A shows the injection phases of the autostop needle of FIG. 9 in accordance with the present disclosure.
Figure 11B:
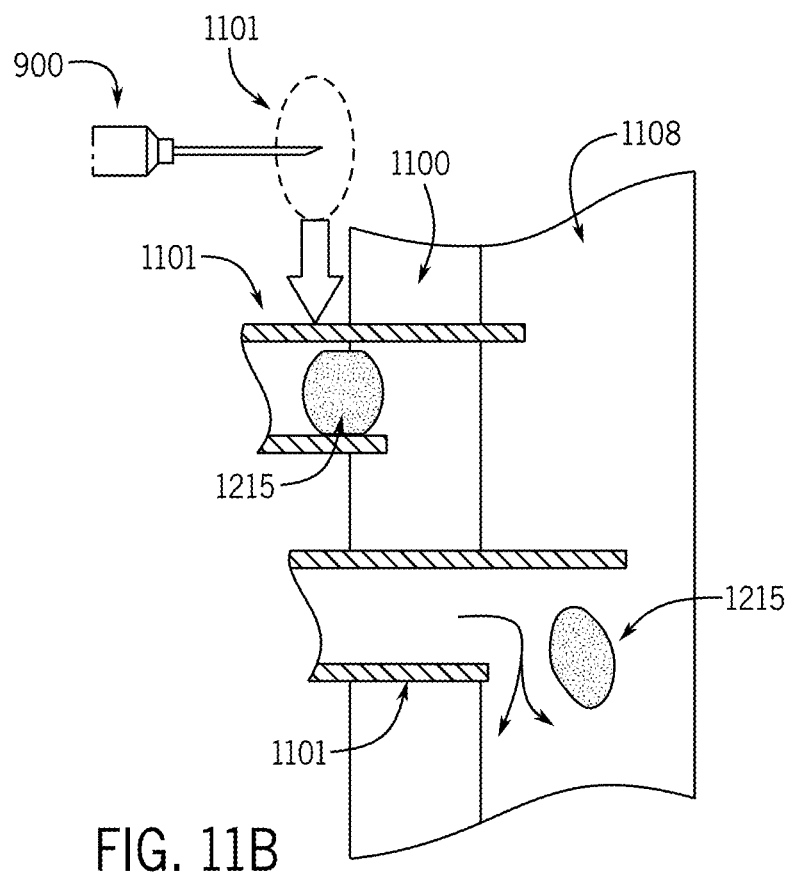
FIG. 11B shows a portion of the injection phases of FIG. 11A in which the autostop needle includes a hydrogel in accordance with the present disclosure.
Figure 11C:
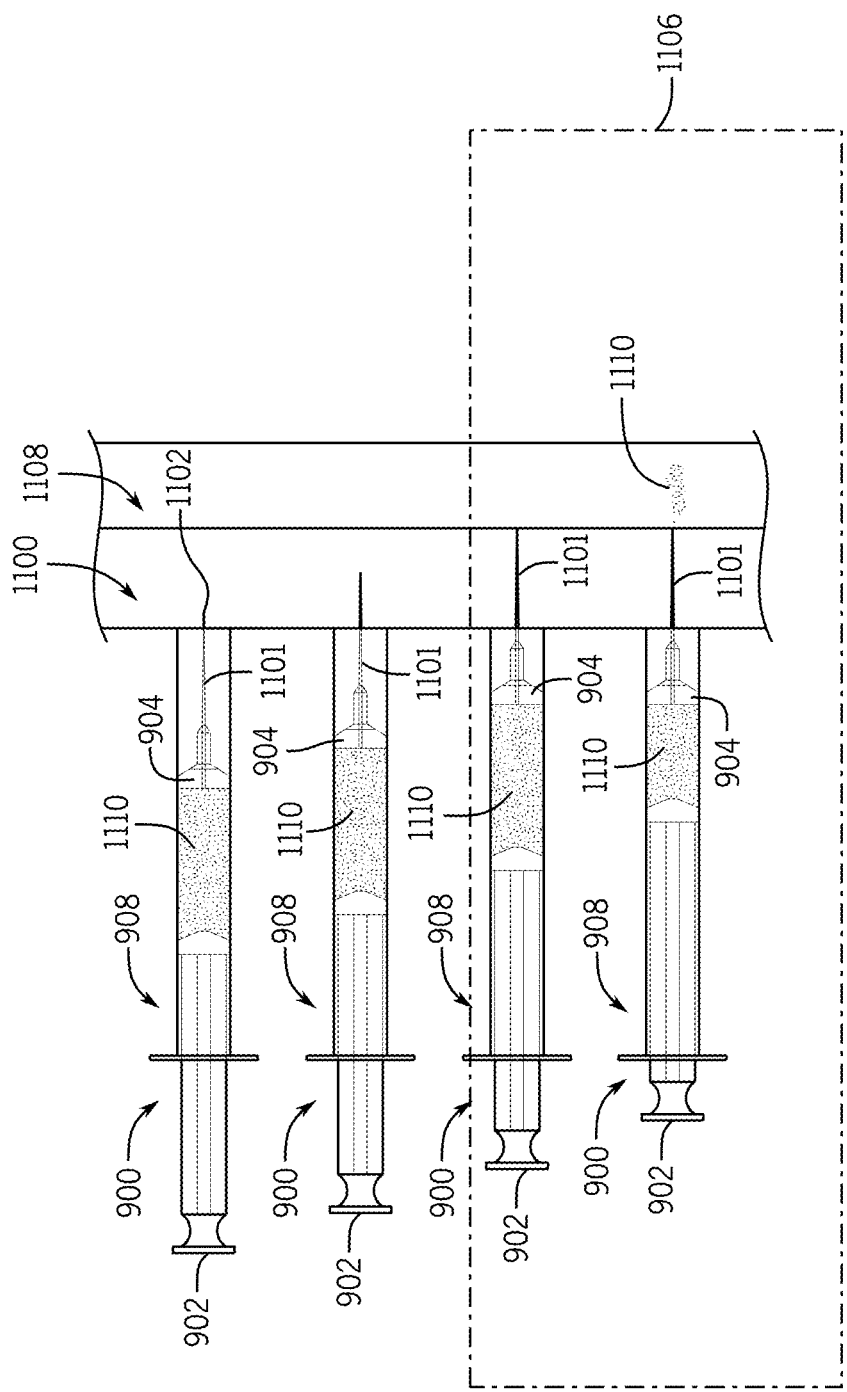
FIG. 11C shows the expanded injection phases of FIG. 11A in accordance with the present disclosure.

In particular, referring to FIGS. 11A-11C, a method of using the above-described autostop needle 900 may be divided into three phases of injection. The autostop needle 900 first enters a tissue 1100 in the initial insertion phase 1102. Upon initial insertion 1102, a tip 1101 of the needle 906 is arranged under the surface of the tissue 1100. As such, any fluid 1110 arranged in the barrel 908 is restricted from exiting the barrel 908 through the needle 906 because the tissue 1100 restricts the opening at the distal end of the needle 906. As a force or a pressure is applied to the plunger 902, a force or pressure is applied to the fluid 1110 in the barrel 908 and thus also to the seal floating 904. However, because the fluid 1110 cannot escape the barrel 908, an opposing force (e.g., the frictional resistance between the floating seal 904 and the barrel 908) is overcome and the floating seal 904 and, thereby, the needle 906 mounted on the floating seal 904 enters further into the tissue 1100, which exemplifies needle penetration phase 1104. This continues until the tip 1101 at the distal end of the needle 906 extends through the tissue 1100 and into a void or cavity 1108, which exemplifies the cavity penetration phase 1106. That is, upon a force or pressure (e.g., some specific amount of force) being applied to the fluid 1110 (and thus also the seal 904), an opposing force (e.g., a frictional force between the seal 904 and the syringe barrel 908) is overcome to cause movement of the floating seal 904 and hollow needle 906 from the second end 912 of the syringe barrel 908 and to extend the distal end 918 with the tip 1101 of the hollow needle 906 into a tissue 1100 of the subject.

Once the tip 1101 of the needle 906 reaches the cavity 1108, the fluid 1110 is no longer restricted against exiting the tip 1101 of the needle 906 and the opposing force (e.g., the resistance between the floating seal 904 and the barrel 908) is sufficient to maintain the current position of the tip 1101 of the needle 906 in favor of fluid 1110 being injected into the cavity 1108 with further pressure or force being applied to the plunger 902. That is, upon the distal end 918 of the hollow needle 906 extending beyond the tissue 1100 of the subject and into the cavity 1108, the system succumbs to the opposing force (e.g., the frictional force between the floating seal 904 and the syringe barrel 908) to displace the fluid 1110 through the opening formed at the distal end 918 of the hollow needle 906 into the cavity 1108. It should be appreciated that the opposing force or forces can include a frictional force between the floating seal and the syringe barrel, a frictional force of the tissue of the subject or a spring based mechanical force (e.g., a spring described with respect to the example of FIGS. 20A and 20B below).

In some aspects, it may be beneficial to have liquid 1110 be a neutral substance. When autostop needle 900 reaches the cavity 1108, it may then be used to drain a substance from the cavity 1108. One non-limiting example of this is a lumbar puncture, where cerebrospinal fluid needs to be collected from a spinal canal (a cavity).

FIG. 11B illustrates an example in which the needle tip 1101 includes a hydrogel plug 1215 that enhances the force or pressure being applied to the fluid or liquid (and hence the seal 904) so as to enable movement of the needle 906 through porous tissues 1100 that exhibit limited resistance to the force being applied. For example, myocardial tissue offers limited resistance to fluid flow and can therefore lead to insufficient applied or driving force, which may cause the needle 906 to remain stationary within the tissue 1100 and fluid to flow into the tissue 1110 rather than into the cavity 1108. In these circumstances, the hydrogel plug 1215 may be located inside the needle tip 1101, to allow a higher internal pressure to be exerted and thereby cause the needle 906 and tip 1101 to move or be driven. Once the needle 906 enters the cavity 1108, the hydrogel 1215 can be expelled or pushed out from inside the needle tip 1101, allowing the fluid to flow into the cavity 1108. The hydrogel plug 1215 may be used in any applications in which an enhanced driving or applied force may be needed or helpful, such as procedures for accessing the abdominal cavity for laparoscopic surgery.

FIG. 11C breaks down the cavity penetration 1106 into two further phases. In a first phase, the autostop needle 900 reaches the barrier between the tissue 1100 and the cavity 1108. At this point, as will be described, the fluid 1110 is still restricted by the tissue 1100 from being dispelled from the barrel 908 through the needle 906. That is, the frictional force between the barrel 908 and floating seal 904 is selected to be overcome by transferring forces applied to the plunger 902 to the fluid 1110, which cannot be compressed or escape the barrel 908/needle 906, and thereby causes advancing movement of the floating seal 904 and, with the floating seal 904, the needle 906. In the second phase, the floating seal 904 and the needle 906 advance sufficiently to cause the tip 1101 of the needle 906 to enter the cavity 1108. Upon the tip 1101 of the needle 906 entering the cavity 1108, the forces or pressure applied to the barrel 908 and, thereby, to the fluid 1110 (and seal 904) cause the fluid 1110 to be expelled from the tip 1101 of the needle 906 into the cavity 1108 because the tip 1101 of the needle 906 is no longer restricted by the surrounding tissue 1100. At this point, the force required to expel the fluid 1110 from the barrel 908, into the needle 906, and from the tip 1101 of the needle 906 is less than the force required to overcome the frictional force between the barrel 908 and the floating seal 904. As such, advancement of the seal 904 and needle 906 mounted therein stops once the tip 1101 of the needle 906 enters the cavity 1108. As such, the autostop needle 900 achieves self-regulation and "autostopping."

Figure 12:
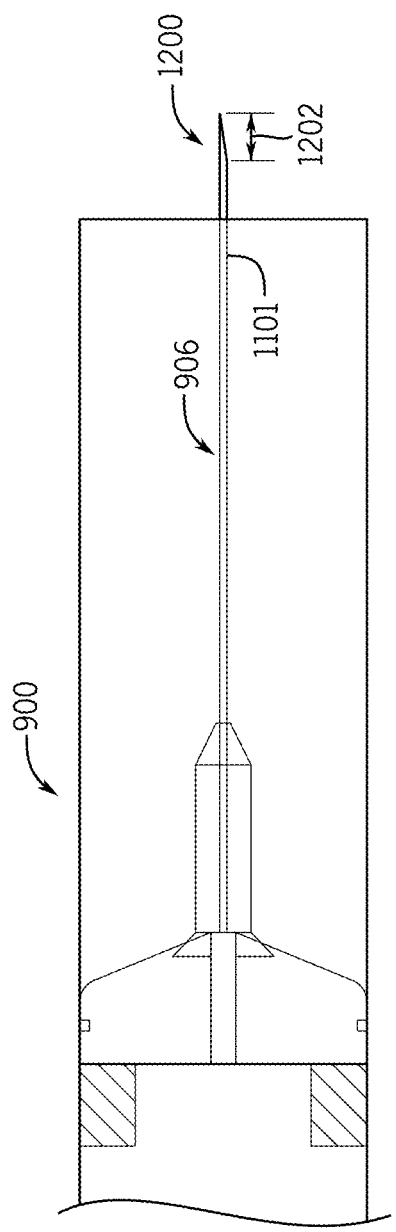
FIG. 12 shows a tip construction of an autostop needle in accordance with the present disclosure.

FIG. 12 highlights another optional aspect of the present disclosure. The tip 1101 of the needle 906 may include a beveled needle tip 1200. The beveled needle tip 1200 may have a predefined beveled length 1202. This aspect may be beneficial when inserting the autostop needle 900 at an angle. The beveled needle tip 1200 can help prevent leaks during the initial insertion 1102 of the autostop needle 900. In certain aspects, it may be beneficial to have a beveled length 1202 within the range of 300 micrometers to 1 millimeter. Alternatively, the beveled length 1202 may have any other predefined length. Additionally, the autostop needle 900 may have a tip with a different shape or design.

Figure 13:
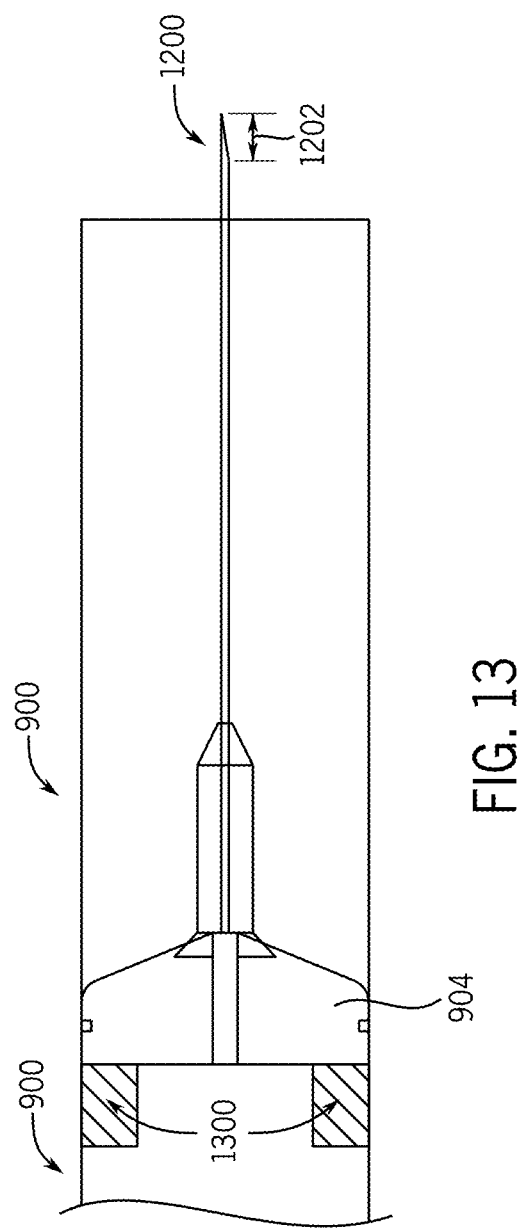
FIG. 13 shows a mechanical blocking feature of an autostop needle in accordance with the present disclosure.

FIG. 13 shows another optional aspect of the present disclosure. The autostop needle 900 may further include a mechanical stop 1300. The addition of the mechanical stop 1300 may help ensure that the floating seal 904 and needle 906 do not move backwards into the barrel 908 during the initial insertion 1102. To achieve this, the mechanical stop 1300 may be mounted to or affixed as part of the barrel 908 and extend into the lumen to physically restrict the floating seal 904 from being displaced beyond the stop 1300.

Figure 14A:
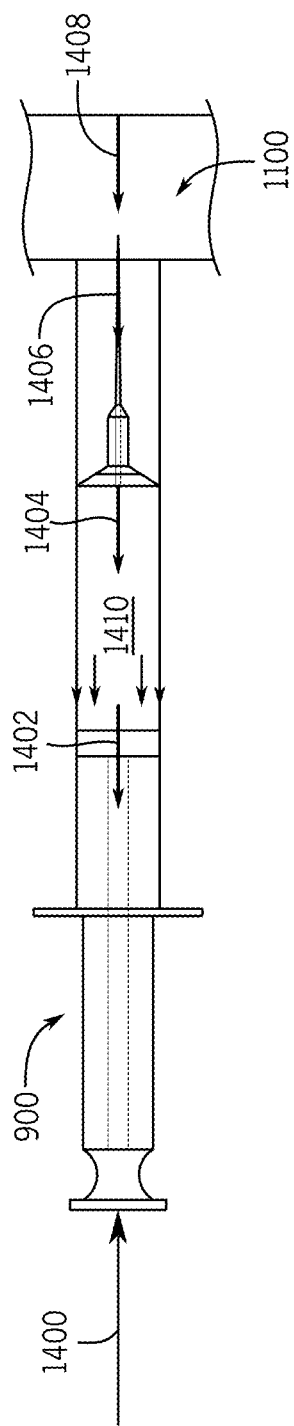
FIG. 14A shows a free body diagram of an autostop needle in accordance with the present disclosure.

To achieve the above-described operation, the autostop needle 900 and the subcomponents may be carefully designed to balance and react to the applied forces as described. FIG. 14A shows a free-body diagram of the autostop needle 900 during the needle penetration phase 1104 to describe the forces during the needle penetration phase 1104. As described, the tip 1101 of the autostop needle 900 is first arranged just within the tissue 1100 as an applied force ($F_{applied}$) 1400 directed to the autostop needle 900 via the plunger 902. Force one ($f_1$) 1402 opposes $F_{applied}$ 1400. Force two ($f_2$) 1404 also opposes $F_{applied}$ 1400. A shear force ($F_{shear}$) 1406 and a cutting force ($F_{cutting}$) 1408 oppose $F_{applied}$ 1400. The internal fluid pressure (Pin) 1410 maintains the shape of the fluid within the autostop needle 900. As such, once the applied force 1400 exceeds a threshold (e.g., a predetermined threshold) equal to the sum of all the opposing forces ($f_1+f_2+F_{shear}+F_{cutting}$), which includes the frictional force between the floating seal 904 and the syringe barrel 908, the floating seal 904 and hollow needle 906 move from the second end of the syringe barrel 908 and the distal end of the hollow needle 906 extends into a tissue of the subject.

Figure 14B:
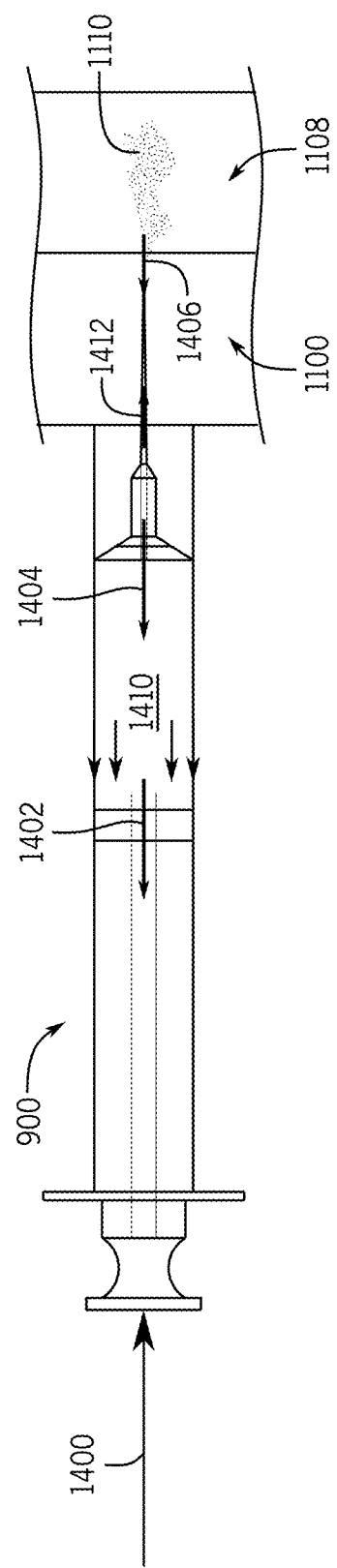
FIG. 14B shows a free body diagram of an autostop needle in accordance with the present disclosure.

FIG. 14B shows a free body diagram of the autostop needle 900 during the cavity penetration phase 1106. An applied force ($F_{applied}$) 1400 is directed to the autostop needle 900. Once the tip 1101 of the autostop needle 900 extends through the tissue 1100 and into the cavity 1108, the second force 1404 between the floating seal 904 and the syringe barrel 908 is sufficient to maintain the floating seal 904 and, thereby, the needle 906 in place and, instead, to displace the fluid 1110 through the opening formed at the distal end of the hollow needle into the cavity. More particularly, force one ($f_1$) 1402 opposes $F_{applied}$ 1400. Force two ($f_2$) 1404 and shear force ($F_{shear}$) 1406 oppose $F_{applied}$ 1400 and the internal fluid pressure (Pin) 1410 maintains the shape of the fluid within the autostop needle 900. However, the cutting force ($F_{cutting}$) 1408 is no longer present, as the autostop needle 900 now fully extends through the tissue 1100. This enables the fluid force ($F_{fluid}$) 1412 as a result of $F_{applied}$ 1400. Liquid 1110 is now able to flow from the tip of the autostop needle 900.

Figure 15:
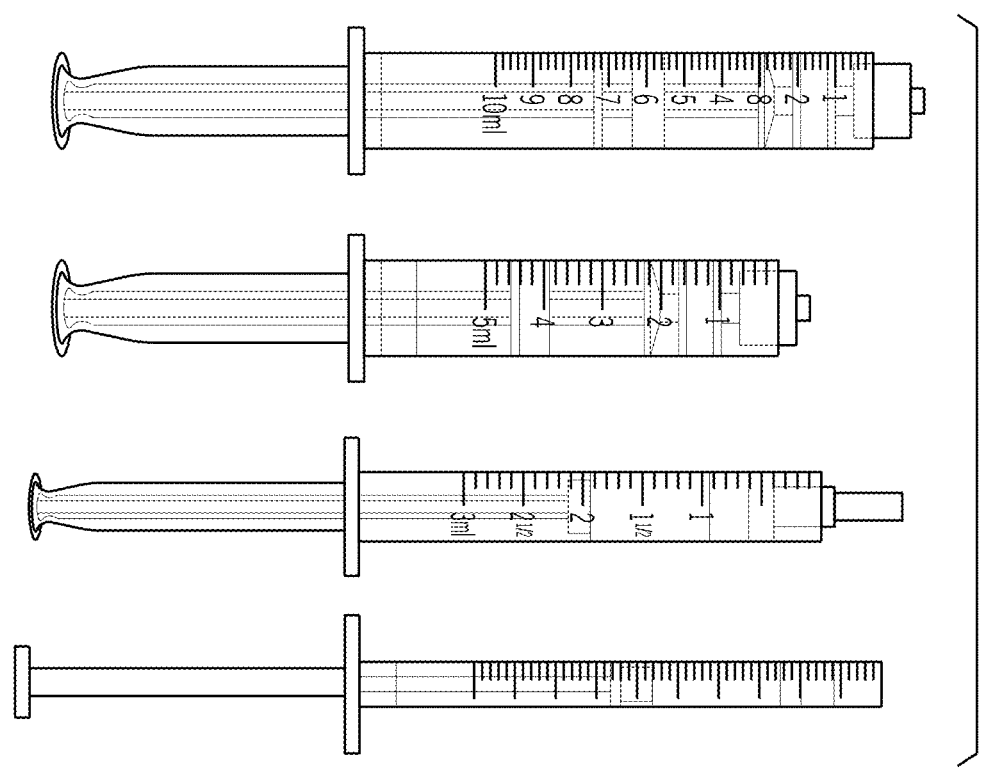
FIG. 15 shows several aspects of an autostop needle in accordance with the present disclosure.

FIG. 15 shows several examples of syringes configured with an autostop needle 900. Different needle sizes, different dosing requirements, different insertion angles, and a multitude of different applications can all utilize the autostop needle 900. Non-limiting examples include syringes of 1 ml, 3 ml, 5 ml, or 10 ml. Of course, as will be described, changes in size, dimension, and the like manifests in different forces being presented and required. The present disclosure recognizes this point and provides systems and methods to balance and calibrate the overall autostop needle 900 to achieve the desired functionality regardless of changes in size, shape, dimension, application, and the like.

Figure 16:
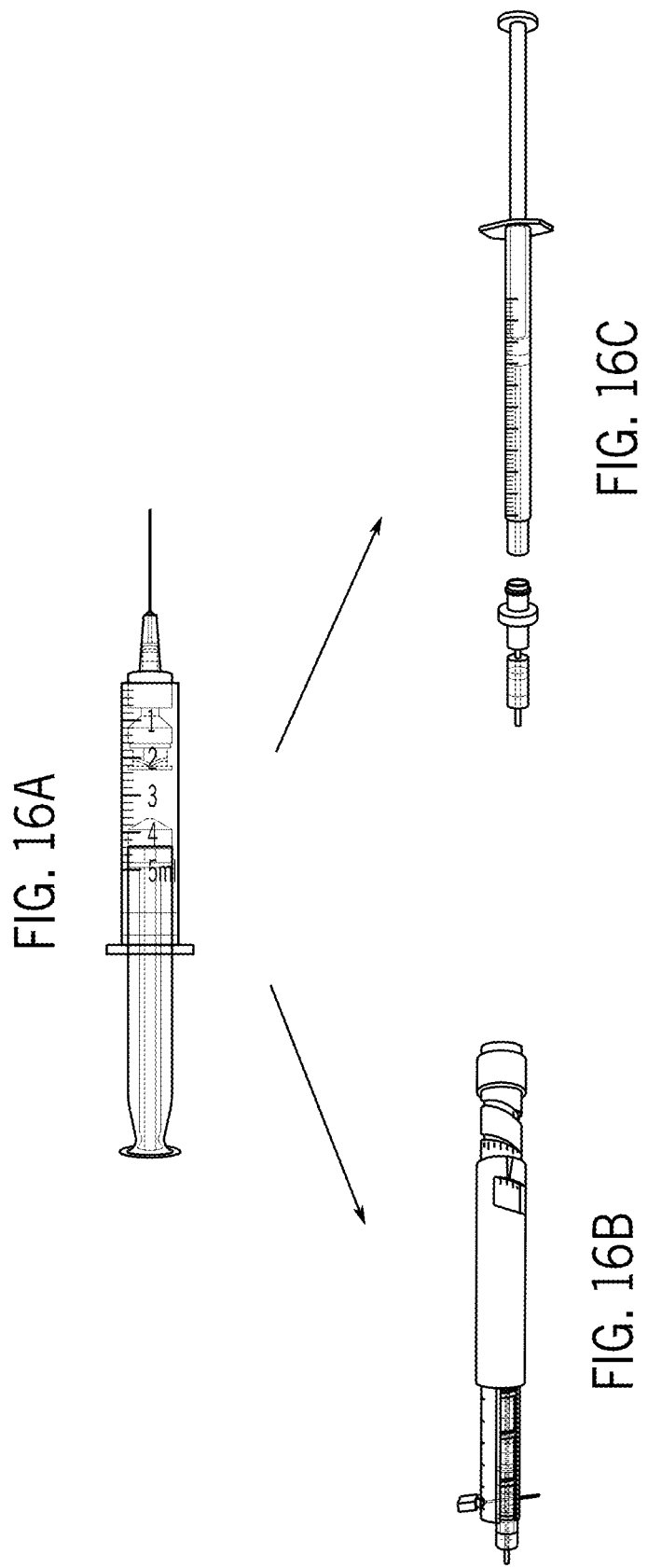
FIG. 16A shows one aspect of an autostop needle in accordance with the present disclosure.
FIG. 16B shows another aspect of an autostop needle in accordance with the present disclosure.
FIG. 16C shows another aspect of an autostop needle in accordance with the present disclosure.

FIGS. 16A-16C show how the autostop needle 900 can be used with various syringes. The design of autostop needle 900 is versatile and can be adapted to multiple configurations. FIG. 16A shows one type of syringe that includes autostop needle 900. FIG. 16B shows a different, one-handed syringe system incorporating the autostop needle 900. The one-handed syringe system may be used, for example, in an insulin pen. FIG. 16C shows a smaller syringe design configured with the autostop needle 900.

Figure 17:
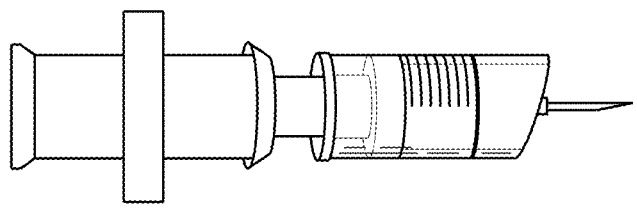
FIG. 17 shows an autostop needle with a separated front chamber in accordance with the present disclosure.

FIG. 17 shows an autostop needle 900 with a separated front chamber. A standard syringe 1700 may be coupled to a connector 1702, such as a luer lock connector. This may enable an autostop module 1704 to maintain a fluidic connection with the standard syringe 1700. A two component module 1706 and a one component module 1708 may also be used. The connector 1702 may be bonded to the autostop module 1704 using epoxy adhesive, or another adhesive commonly known in the art. If the diameter of the connector 1702 is larger than that of the syringe barrel 908, the needle may be directly bonded to the plunger 902. It should be appreciated that other suitable fluidic connectors different from connector 1702 may be used in accordance with the present disclosure. In certain aspects, the tip of the syringe barrel 908 may be machined off to enable movement of the autostop module 1704 inside the barrel 908.

Figure 17A:
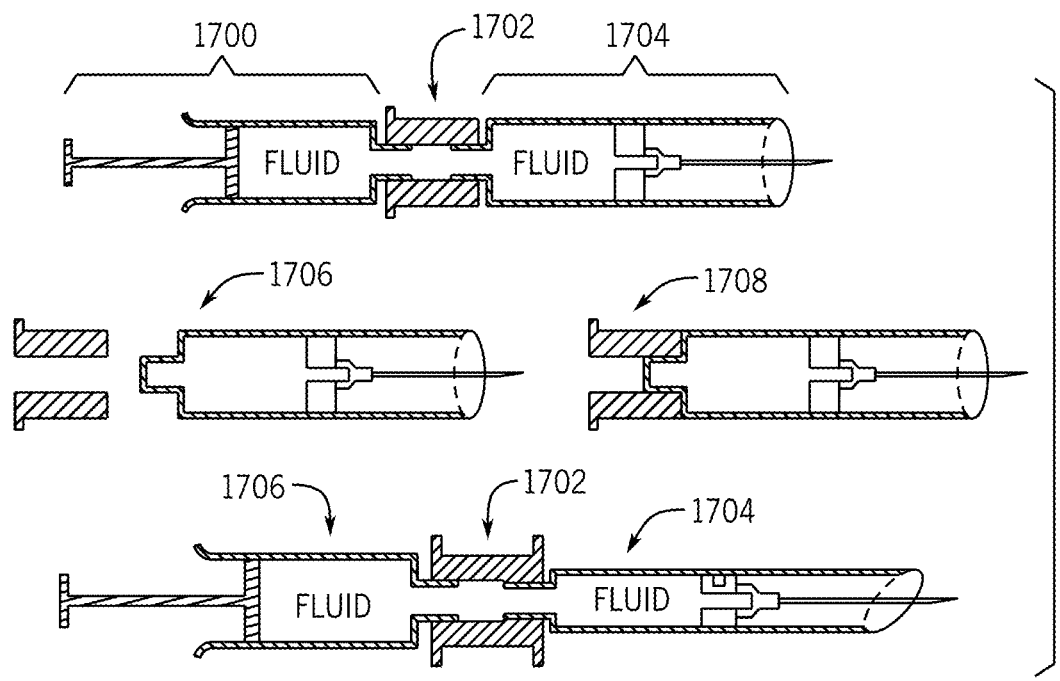
FIG. 17A shows another autostop needle with a separated front chamber and a reduced diameter in accordance with the present disclosure.

FIG. 17A shows another example of the autostop needle 900 with a standard syringe 1700, connector 1702 and autostop module 1704. The autostop module 1704 of FIG. 17A includes a plunger 902 having a reduced or smaller diameter for reducing the variability in dead volume, which can reduce errors introduced by such dead volume.

Figure 18:
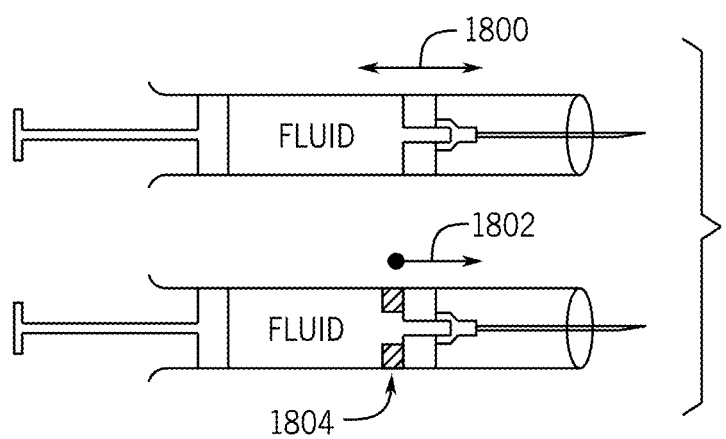
FIG. 18 shows an autostop needle with a back support in accordance with the present disclosure.

FIG. 18 shows another aspect of the autostop needle 900. A movable plunger 1800 may be used alone. Alternatively, a back support 1804 may be included, resulting in an exclusively forwardly movable plunger 1803. The back support 1804 can restrict the motion of a needle plunger while initial insertion 1102 occurs.

Figure 19:
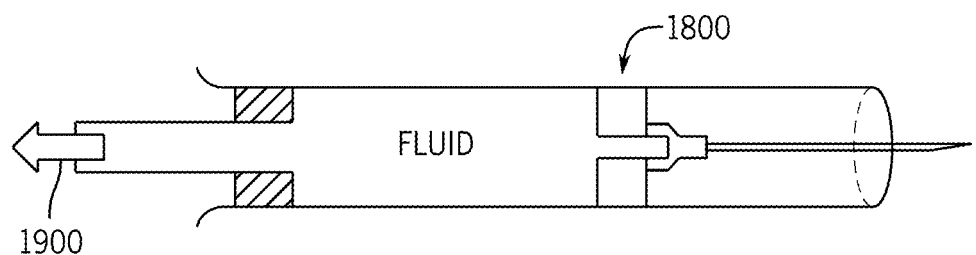
FIG. 19 shows a remote pressurized system connected to an autostop needle in accordance with the present disclosure.

FIG. 19 shows another aspect of the autostop needle 900. A movable plunger 1800 may be positioned within the autostop needle 900. The autostop needle 900 may be in fluid connection with an external pressure source 1900, which may control the movement of the movable plunger 1800 during initial insertion 1102, needle penetration 1104, and cavity penetration 1106.

Figure 20A:
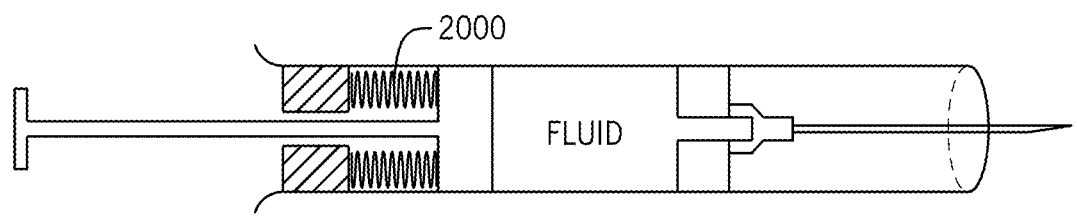
FIG. 20A shows a compressed spring loaded autostop needle configuration in accordance with the present disclosure.
Figure 20B:
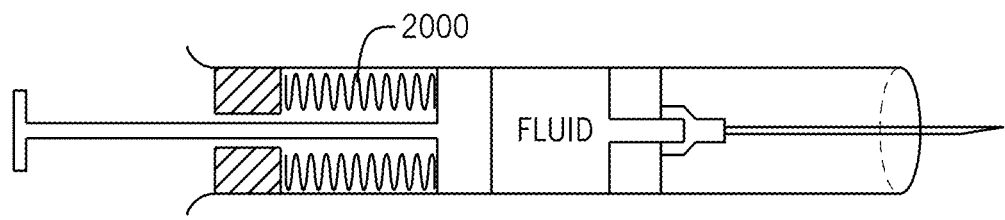
FIG. 20B shows an expanded spring loaded autostop needle configuration in accordance with the present disclosure.

FIGS. 20A and 20B show another aspect of the autostop needle 900. A spring 2000 may be included in autostop needle 900 to restrict and enable, when appropriate, the movement of the movable plunger 1800. The spring 2000 may expand and contract.

Figure 21:
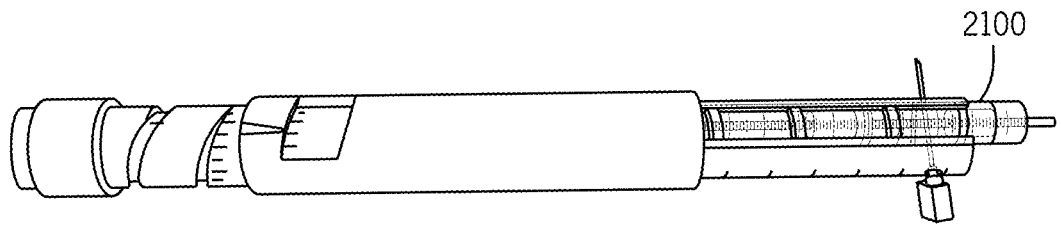
FIG. 21 shows a modified insulin pen in accordance with the present disclosure.
Figure 22:
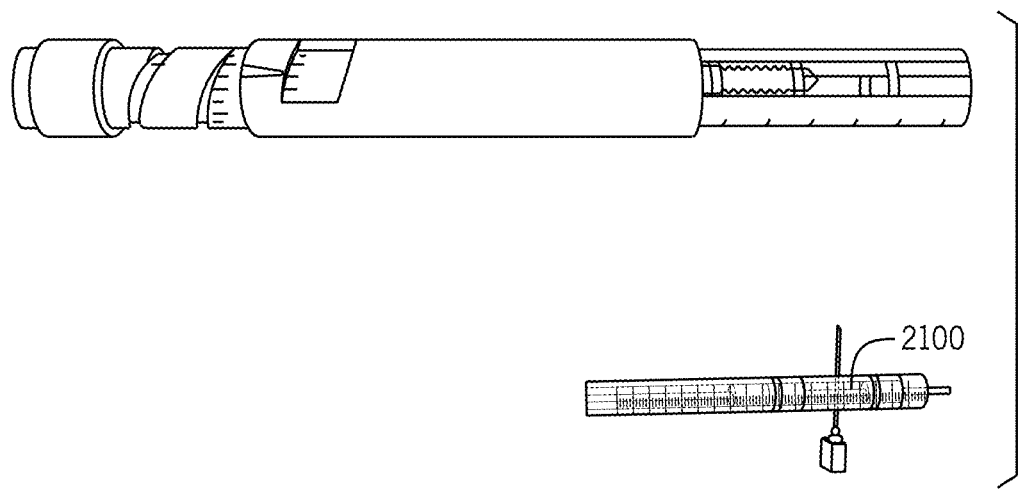
FIG. 22 shows a modified insulin pen module in accordance with the present disclosure.

FIGS. 21 and 22 show another aspect of the autostop needle 900. The autostop needle 900 may be configured as a modifier tip 2100 to be retrofit with an existing insulin pen. The modifier tip 2100 can be removable from the insulin pen.

As described, the autostop needle 900 can have a wide variety of applications and can be used in multiple tissues. Some potential applications include, but are not limited to, suprachoroidal space injections, epidurals, lumbar punctures, skin injections, and injections performed using a robot, and some tissues include skin, muscle and vessel wall to target cavities (or less dense tissue).

The present disclosure has been described in terms of one or more aspects or alternatives, and it should be appreciated that many equivalents, alternatives, variations, and modifications, aside from those expressly stated, are possible and within the scope of the disclosure.

The present disclosure can be further understood by way of the following non-limiting examples.

EXAMPLES

Example 1. Measuring the Drag Force on the Needle During Injection

Figure 23:
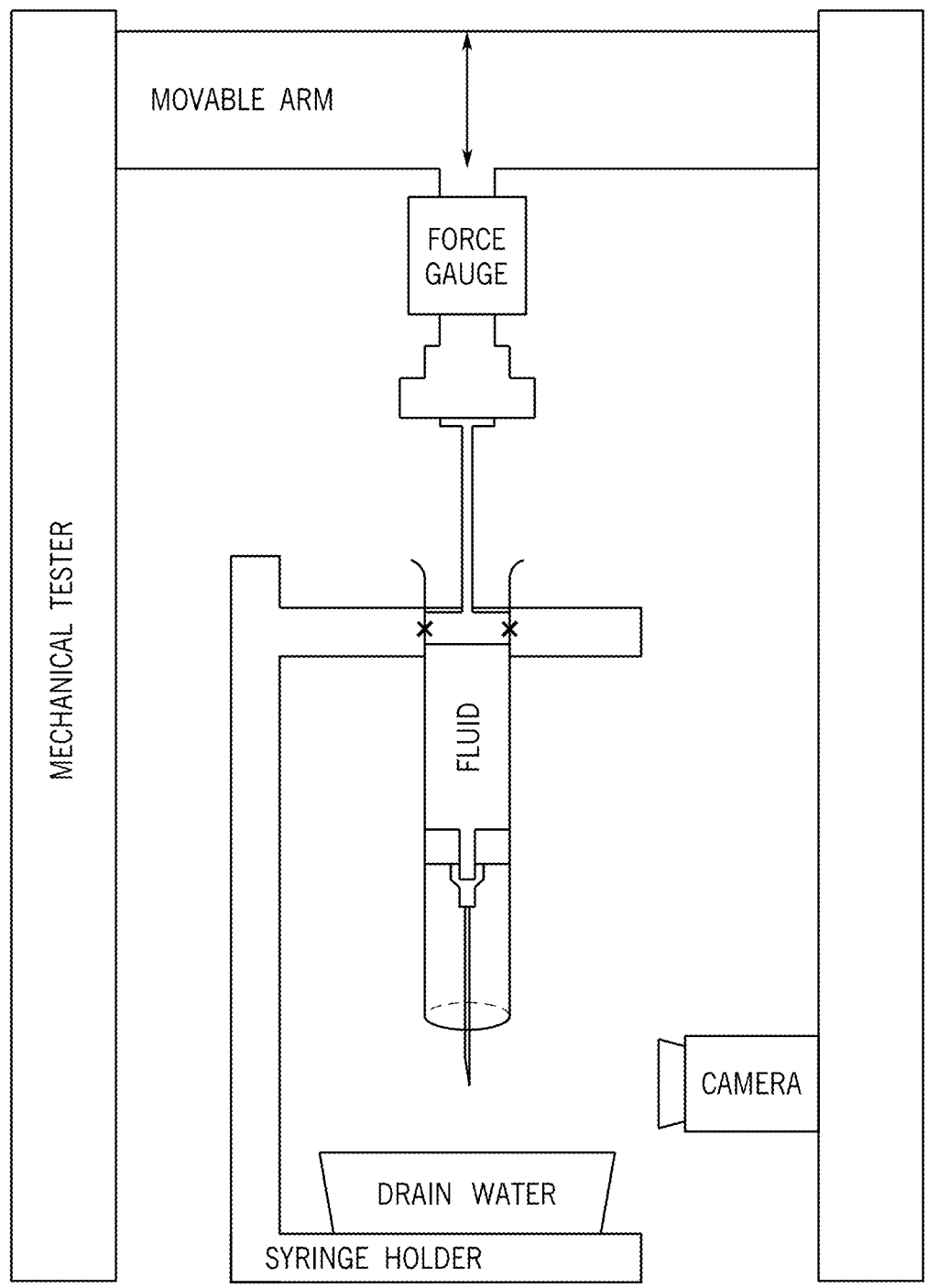
FIG. 23 shows an experimental set up used to measure drag force on a needle during injection.

FIG. 23 shows the schematic for an experimental setup to measure the threshold flow rate $Q_t$. The threshold flow rate $Q_t$ is defined by the minimum flowrate (q) needed to enable needle movement inside the cavity 1108. The autostop needle 900 is mounted on a mechanical tester such that the barrel 908 is held in position while the plunger 902 and needle 906 are free to move. The upper arm of the mechanical tester pushes the plunger 902 at a given constant speed which results in a known flow rate. Applied force 1400 is monitored continuously and a video camera records the motion of the needle 906. The flow rate at which the needle 906 starts moving is noted as the threshold flow rate $Q_t$.

Figure 26:
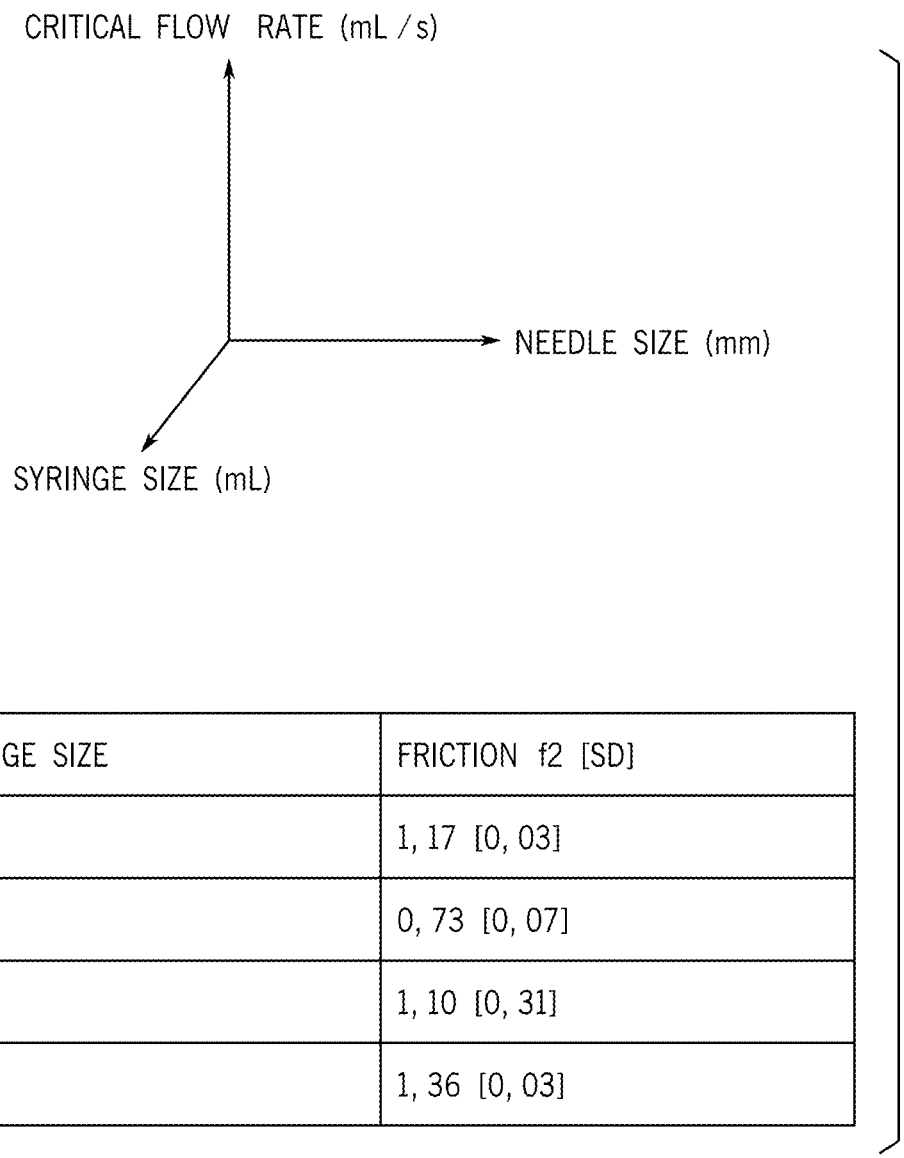
FIG. 26 shows a relationship between syringe size and friction magnitude in accordance with the present disclosure.
Figure 27A:
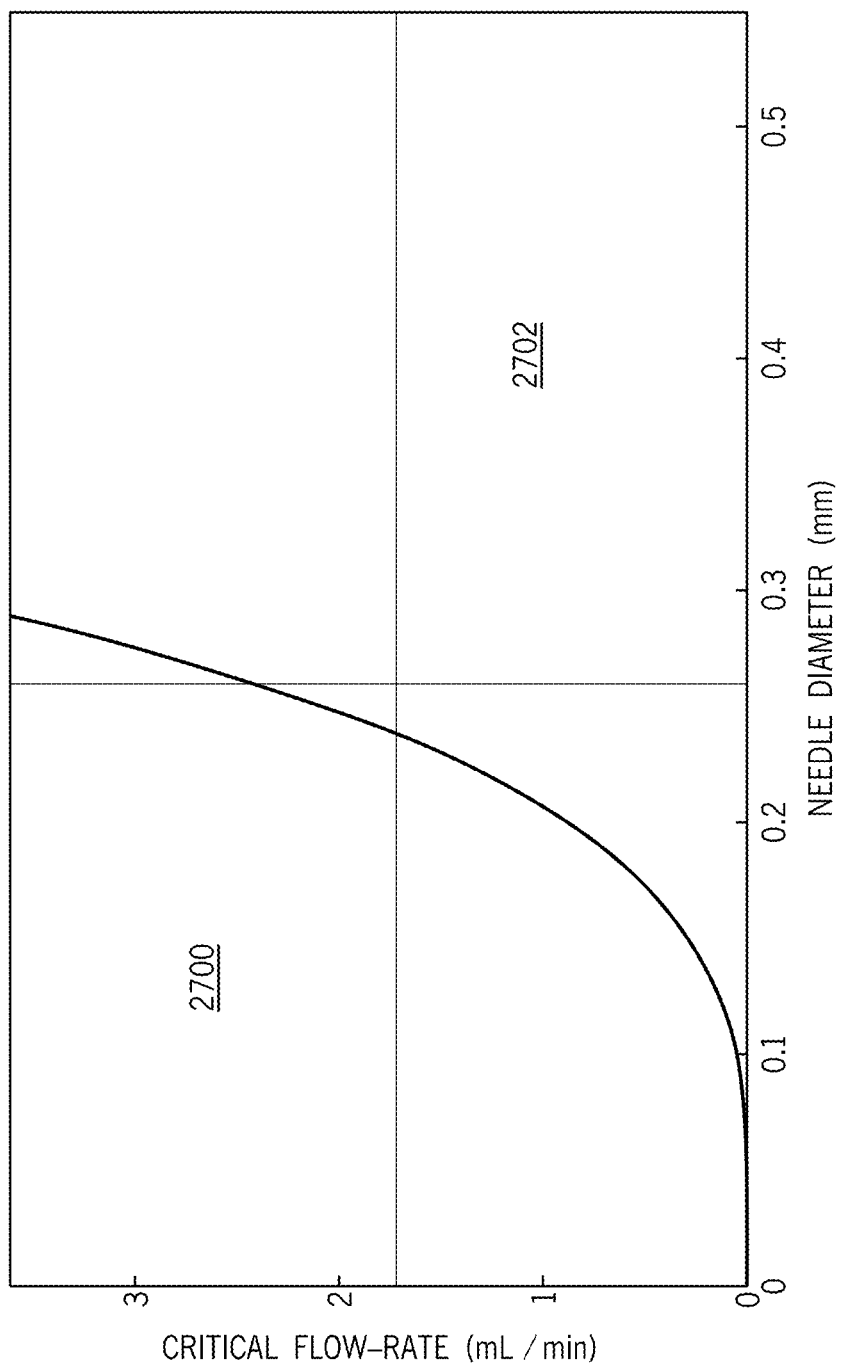
FIG. 27A shows an injection model for various needle diameters in accordance with the present disclosure.
Figure 27B:
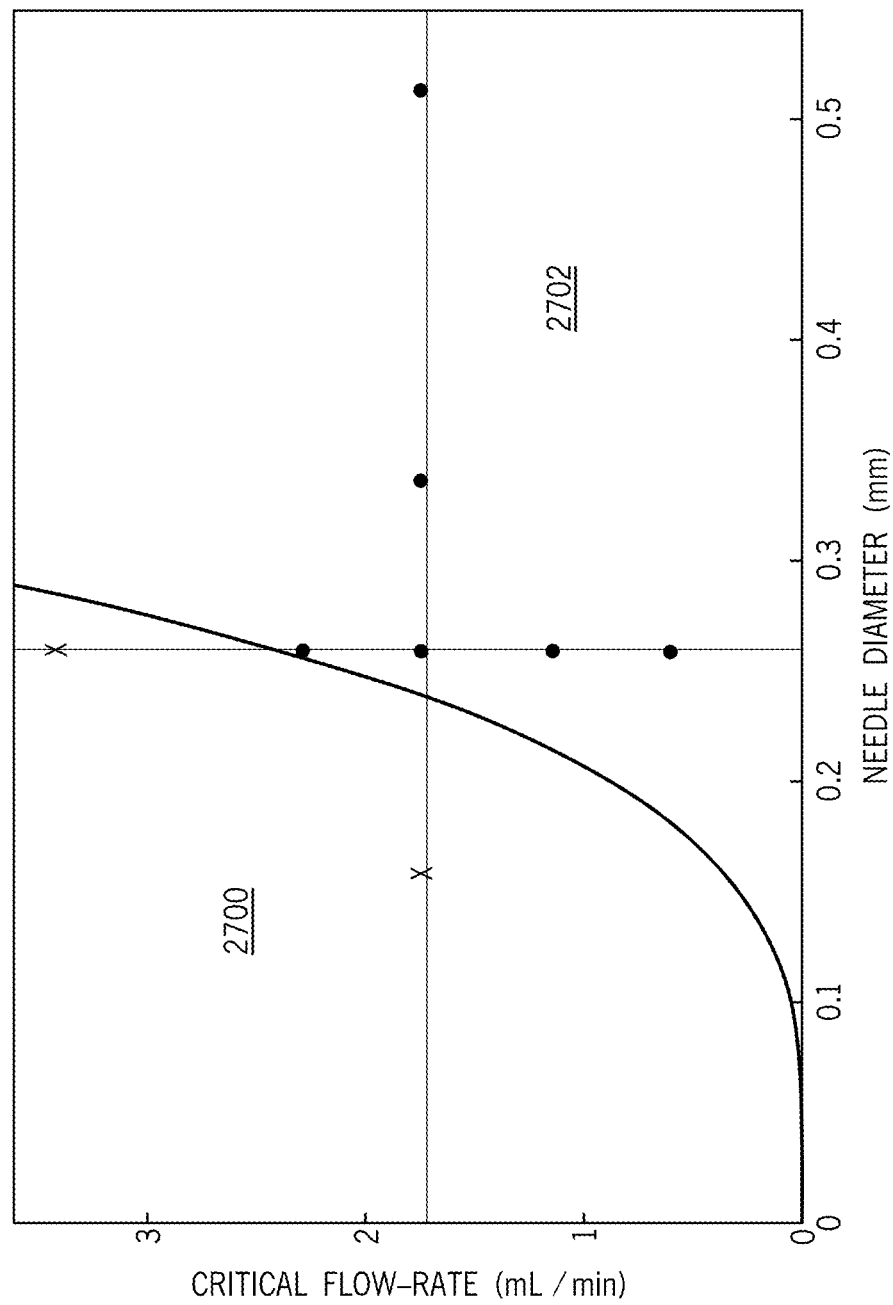
FIG. 27B shows the model of FIG. 27A with experimental data according to the present disclosure.

FIG. 27A is a graph showing modeling of the threshold flow rate plotted as a function of the inner diameter of the needle 906. The plot is divided into a failure region 2700 and a safe region 2702. FIG. 27B shows the data points collected during experimental verification. The results show that it is possible to reliably predict success and failure of the autostop needle 900 and, thus, select flow rates for a given needle diameter and, thereby, forces and materials to achieve the desired parameters in the safe region 2702. In this non-limiting example, hypodermic needles are referred to by their gauge number (G7 to G34) indicating their inner diameter. The curve plotted indicates the maximum admissible flow-rate calculated for a 5 mL syringe size and zero external shear force 1406 ($F_{shear}=0$). The analytical model allows one to determine a safe configuration (syringe size, needle size, injection flow-rate) of the autostop needle 900. To this point, FIG. 26 illustrates that flow rate control can be achieved to avoid the needle 906 moving within the cavity 1108.

Example 2. Suprachoroidal Space Injection Technique

Figure 24:
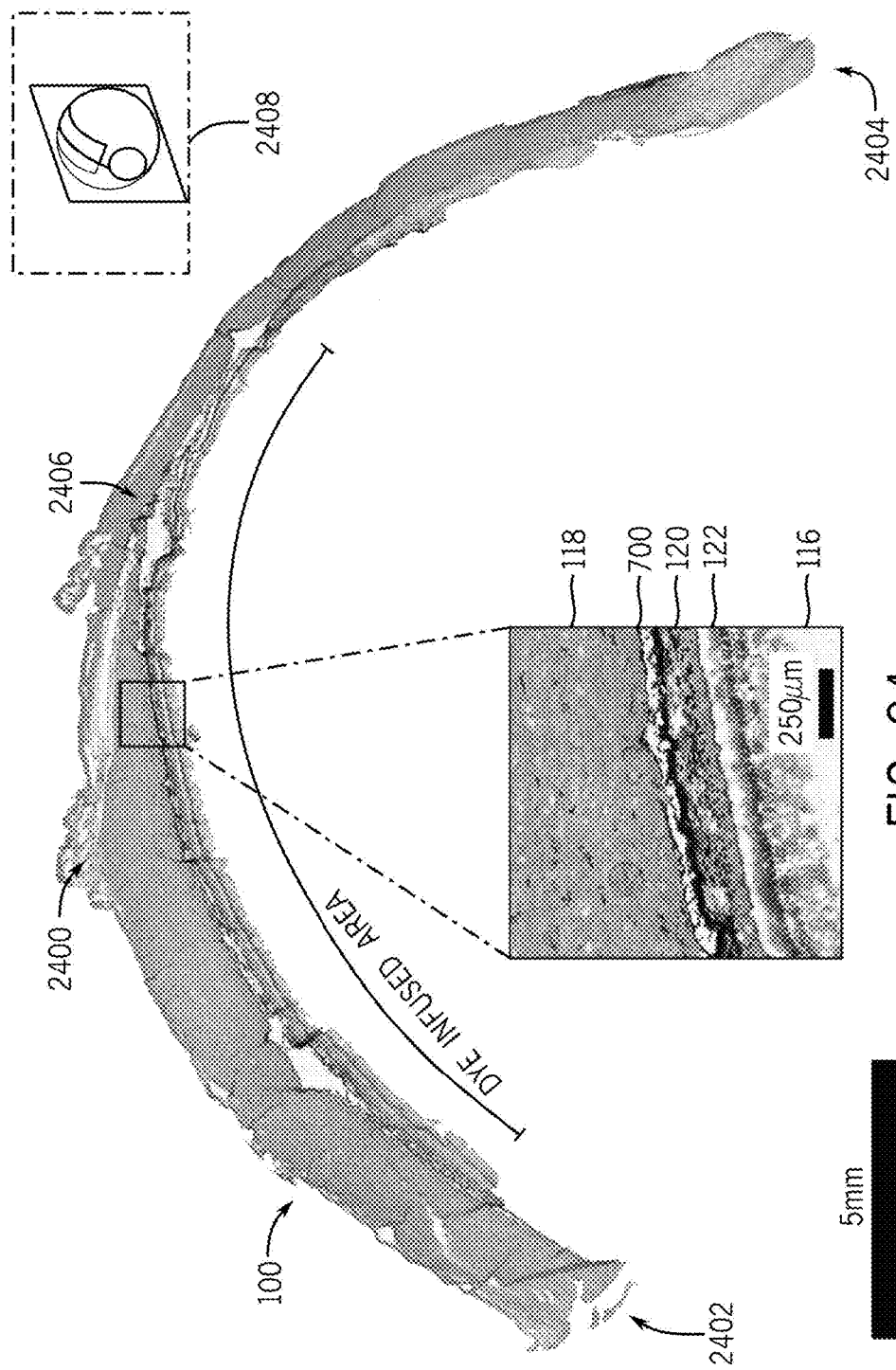
FIG. 24 shows the method of using an autostop needle with an eye in accordance with the present disclosure.

FIG. 24 illustrates a suprachoroidal space injection technique. The eye 100 is penetrated at entrance point 2400 by the autostop needle 900. The autostop needle 900 advances in the eye tissue to the injection point 2406. The eye 100 is shown on a sagittal plane 2408, where both the eye front 2402 and eye back 2404 are captured. The injected green dye can be seen throughout the suprachoroidal space 700. As shown, the other layers (sclera 118, choroid 120, retina 122, and vitreous humour) remain free of the injected green dye.

Example 3. Results of a Cavity Injection Via Autostop Needle

Figure 25:
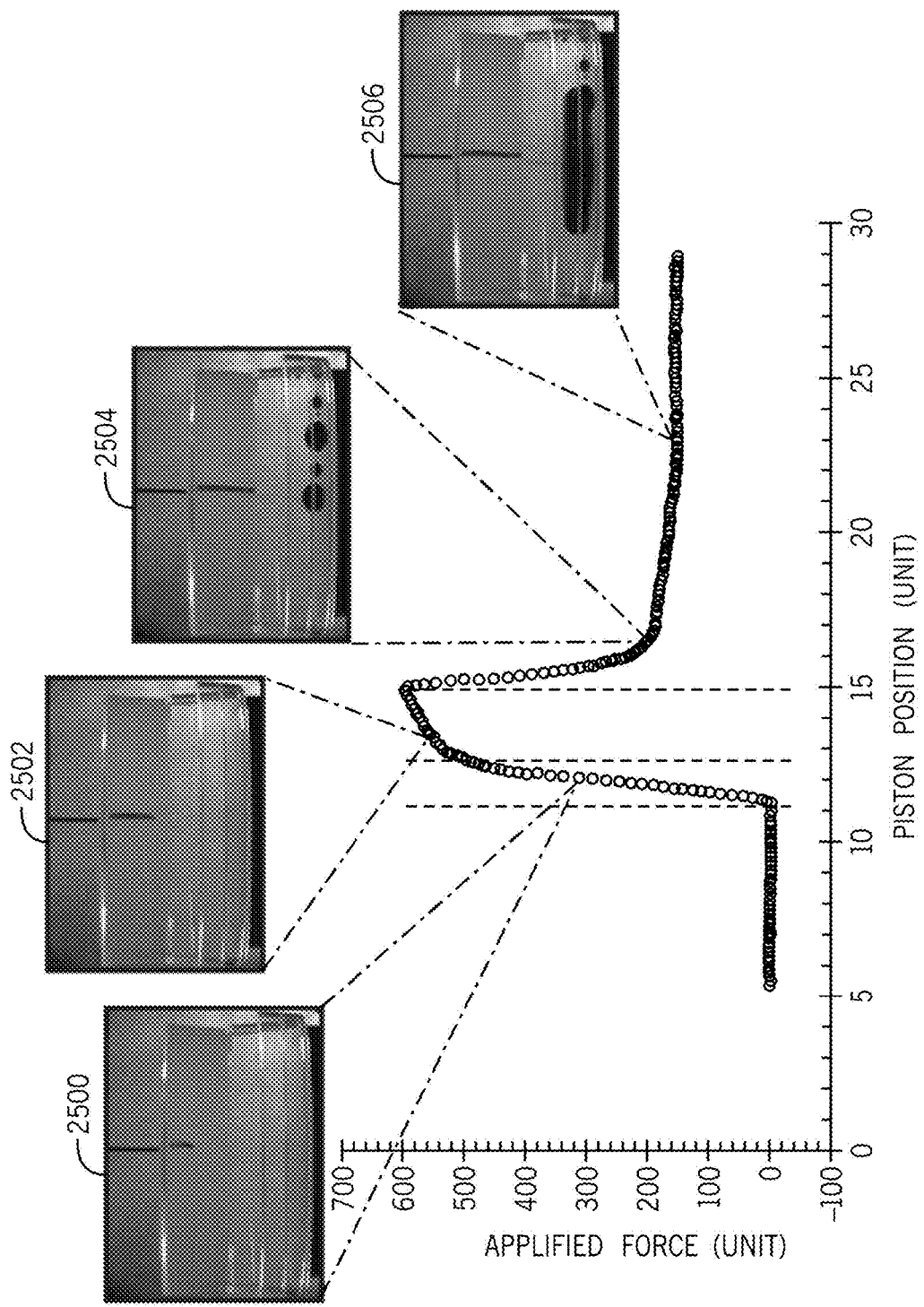
FIG. 25 is a representative plot showing force measurements while an autostop needle is inserted in accordance with the present disclosure.

FIG. 25 is a graph showing test the results of injecting a fluid through a block of soft polymer using an autostop needle. To demonstrate the auto-stop feature of the syringe, colored water was injected through a PDMS block while monitoring the applied force on the plunger using a mechanical tester. The needle was first advanced into the PDMS wall to block the fluid flow through the needle. Frictional force on the rubber seal is sufficient to restrict the needle from moving back during the pre-insertion into PDMS wall. Then a force was applied on the plunger that leads to movement of the needle through PDMS as expected.

FIG. 25 shows a typical profile of the force applied on the plunger as it is displaced at a constant speed using the mechanical tester. Corresponding position of the needle inside PDMS block is shown in inset images of FIG. 25. Applied force is measured as zero before the arm of mechanical tester contacts the plunger. Then the force increases until both the needle and the plunger start moving. This force should be sufficient to overcome frictional forces of the rubber seals and the force of insertion on the needle. Force of insertion includes two parts; one is at the tip while the second force is the shear force applied by surrounding tissue. As the needle moves deeper into the tissue, the contact area between the tissue and needle increases and results in higher force of insertion. This rise is observed in the applied force as the linearly increasing portion of the profile after the sharp rise. A sharp drop in force is observed as the needle tip reaches the cavity since the opposing force quickly diminishes. As the fluid is injected, applied force remains constant. The progress of the needle can be seen by the first piston position 2500, the second piston position 2502, the third piston position 2504, and the fourth piston position 2506.

Example 4. Comparing a Regular Needle with an Autostop Needle

Figure 28A:
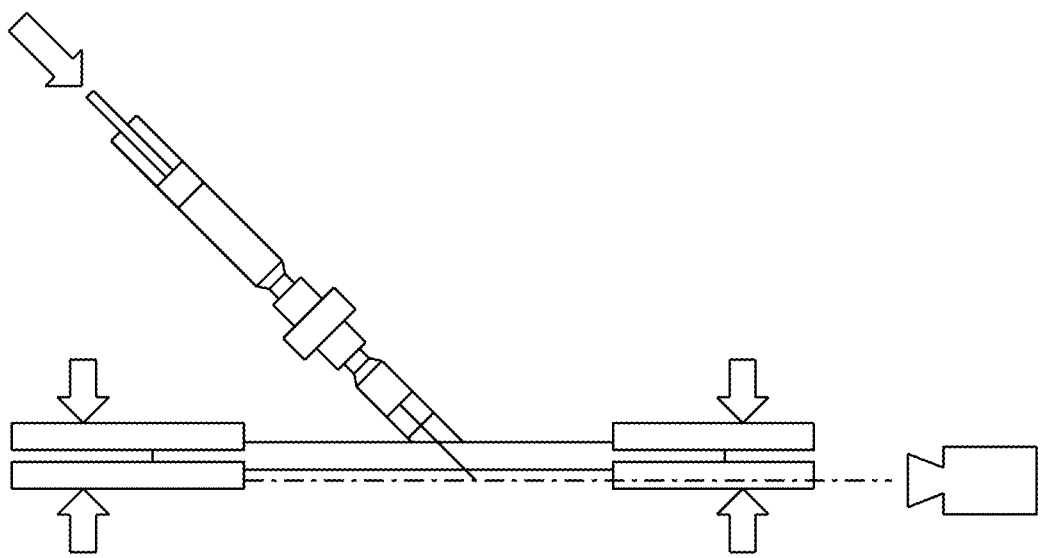
FIG. 28A shows an autostop needle injection in accordance with the present disclosure.
Figure 28B:
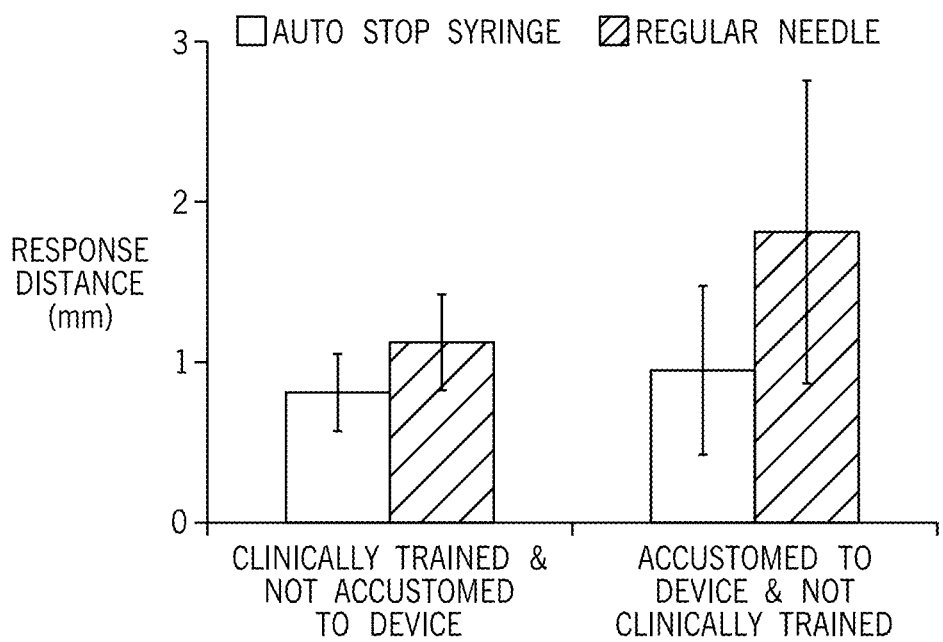
FIG. 28B shows a skills comparison between a regular needle and an autostop needle.

FIGS. 28A and 28B show the technique and results of a cavity injection with a regular needle and an autostop needle. In both instances of the clinically trained and not clinically trained, there was a reduction in response distance when the autostop needle was used instead of the regular needle.

Figure 29:
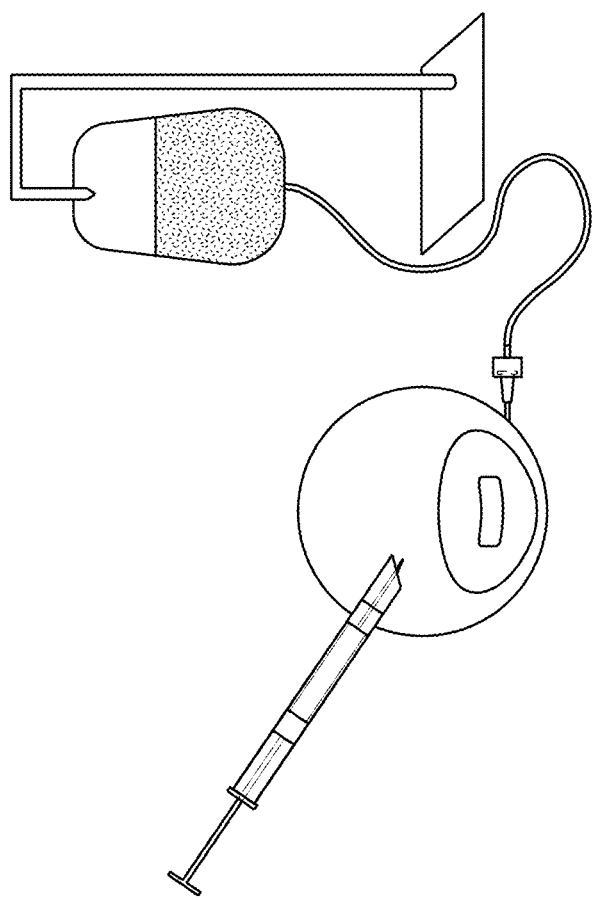
FIG. 29 shows an eye injection in accordance with the present disclosure.

FIG. 29 shows the technique and results of a suprachoroidal space injection with a regular needle and an autostop needle. A qualitative experiment includes injecting a dye-colored fluid into the SCS of enucleated cow eyes was performed, as shown by FIG. 29.

Example 5. Autostop Needle Results for the Suprachoroidal Space

Figure 30A:
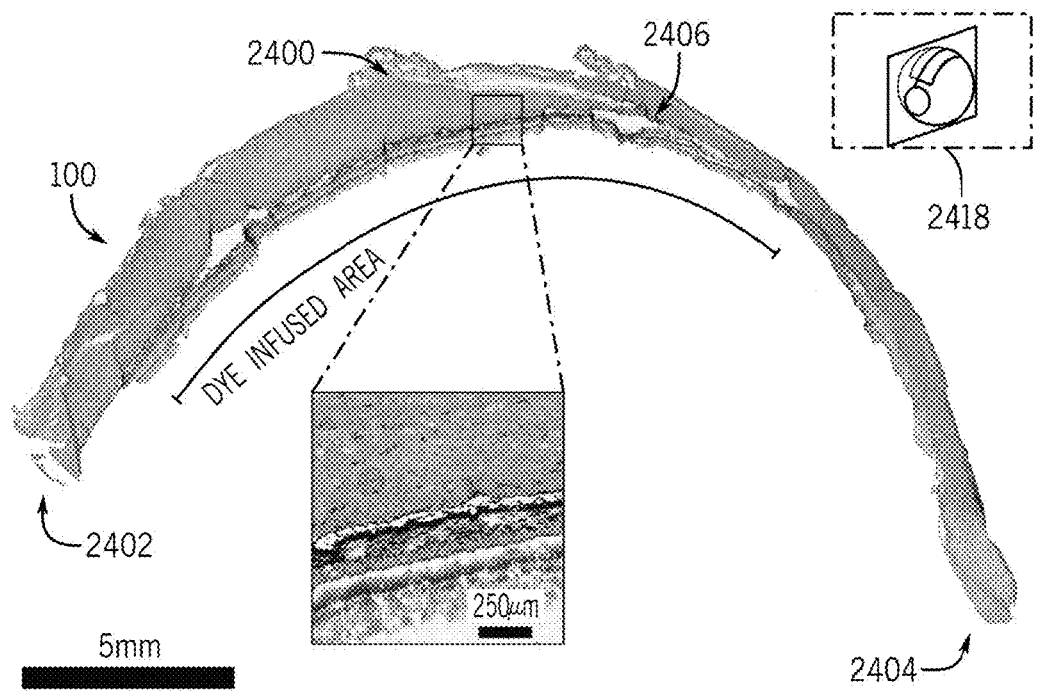
FIG. 30A shows an eye post-injection as the dye and the needle track.
Figure 31:
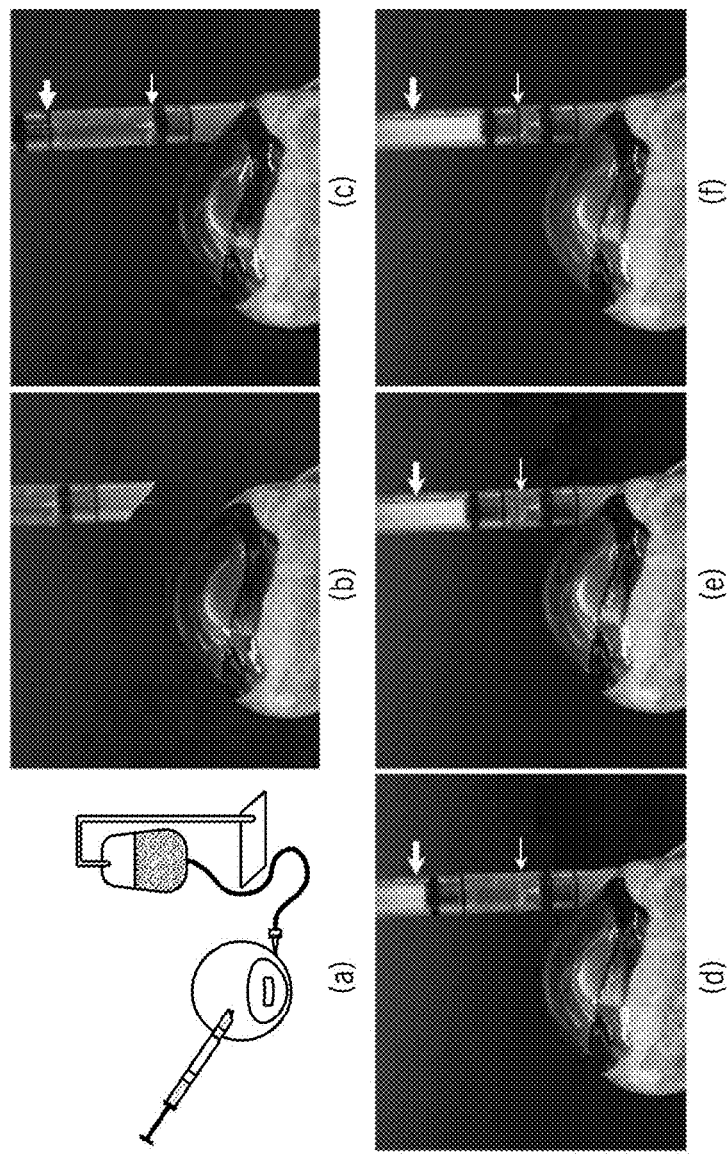
FIG. 31 shows the experimental setup for ex-vivo eye injections in accordance with the present disclosure.

The autostop needle was used to perform an injection of colored water into the suprachoroidal space of enucleated cow eyes. FIGS. 30A and 31 show the pictures taken during suprachoroidal injection using an autostop needle as well as the results of the injection. Eyes were secured in place and pressurized using a water column (a). The needle tip was pre-inserted in scleral tissue to block fluid flow and plunger was pushed continuously. The needle moves initially and stops on its own. Since the plunger is pushed continuously fluid is delivered when the needle stops moving. Since suprachoroidal space is the first cavity encountered by the needle tip, the fluid should be delivered in that space. Referring to (b)-(f) of FIG. 31, a series of images are shown with plunger motion. Thick and thin arrows point to the original position of the plunger and needle base in all the images.

Figure 30B:
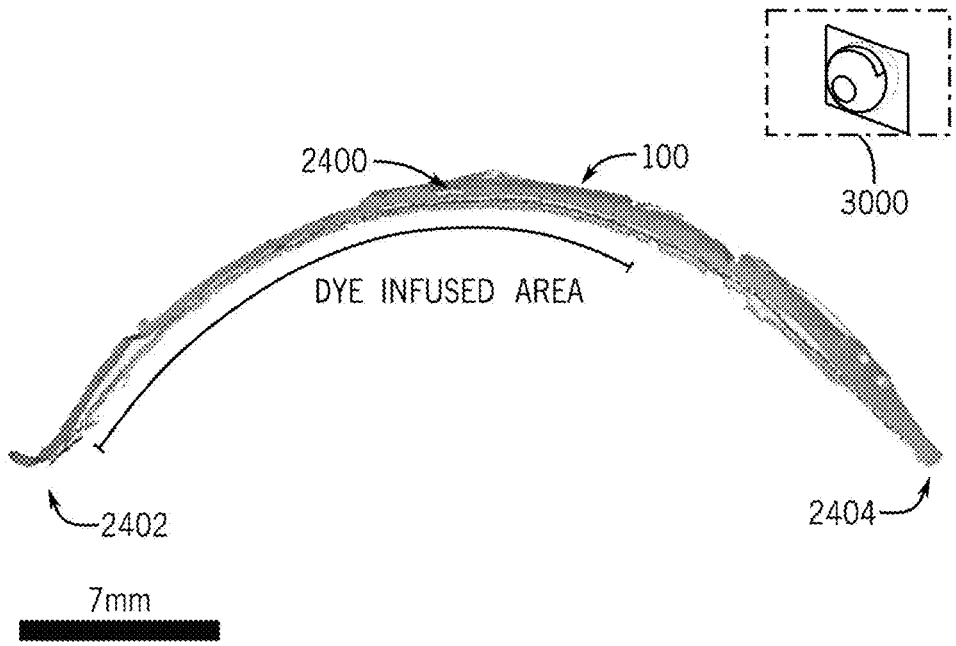
FIG. 30B shows the SCS after the eye injection of FIG. 30A in accordance with the present disclosure.

To mimic clinical settings, several injections were performed using a single hand to secure the eye and the other hand to operate the autostop needle. The eye was cryosectioned to observe the location of dye after each injection. FIG. 30A-30B show sections of the eye having the dye present in between the sclera and choroid. FIG. 30B shows an alternate view via the coronal plane 3000.

Example 6. Injection of Cells Using an Autostop Needle

Figure 32A:
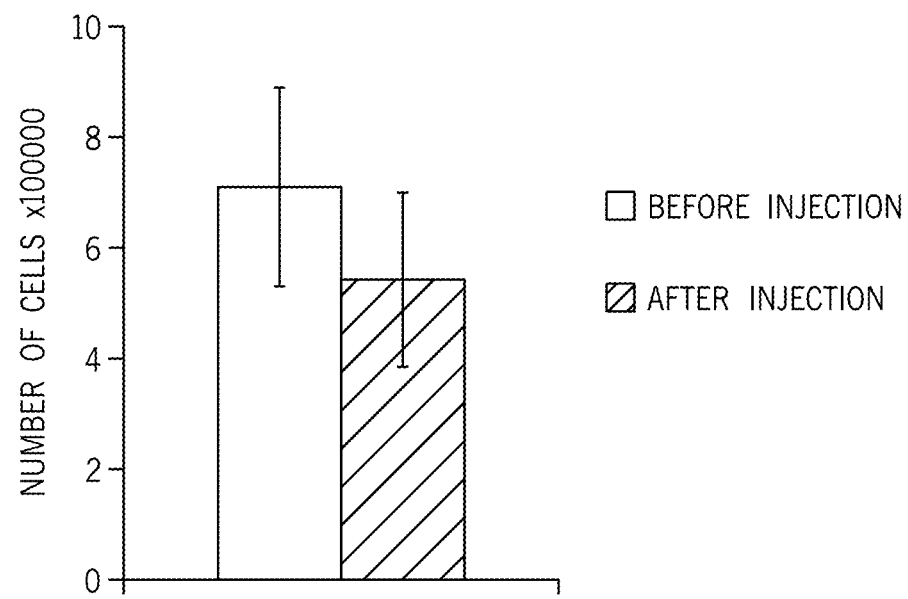
FIG. 32A shows the change in the number of cells after an autostop needle injection in accordance with the present disclosure.
Figure 32B:
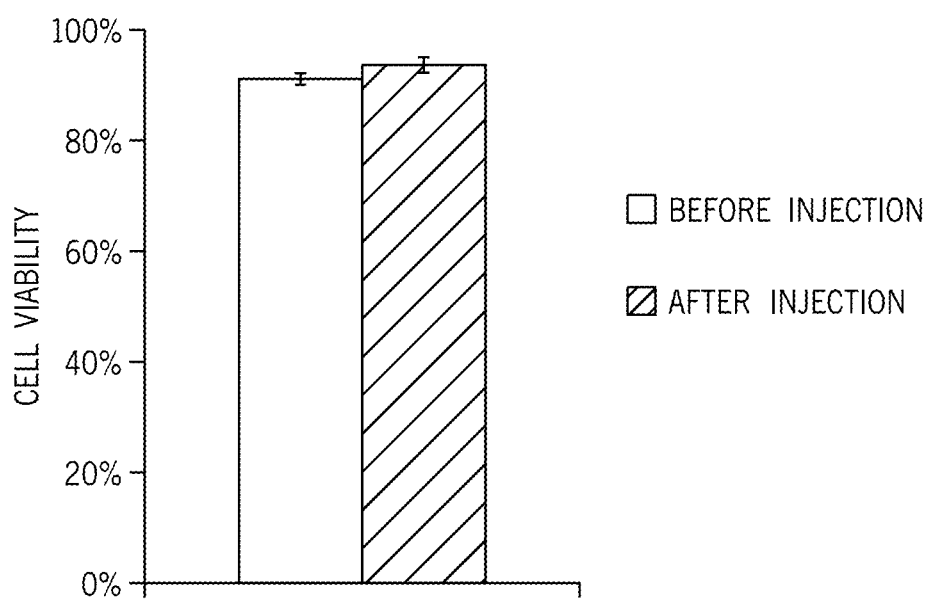
FIG. 32B shows the change in cell viability after an autostop needle injection in accordance with the present disclosure.

FIGS. 32A and 32B show the results of injecting neutrophils using a 30 G autostop needle. The number of cells is shown before and after the injection, as well as the cell viability before and after the injection.

Example 7. Needle Overshoot Comparison for Regular and Autostop Needles

Figure 33:
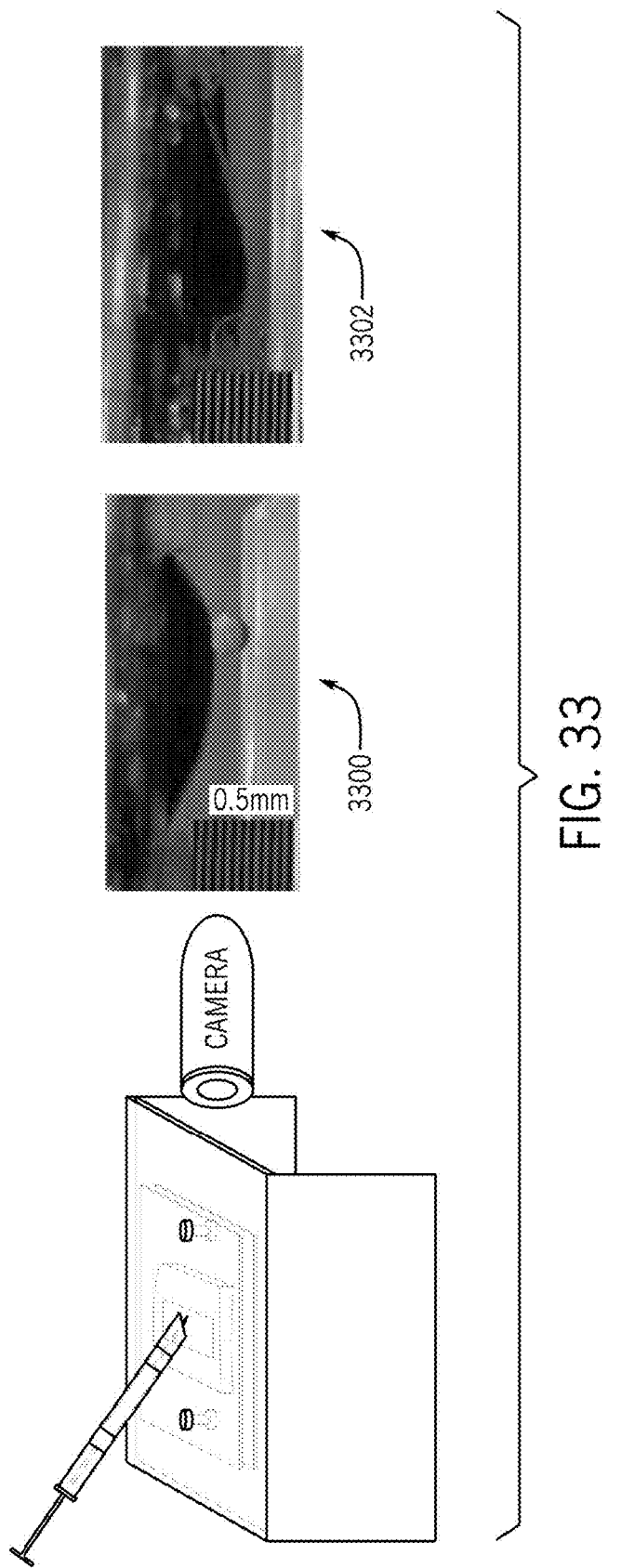
FIG. 33 shows the experimental difference between an autostop needle injection and a regular syringe injection, as performed by a clinician, in accordance with the present disclosure.

Overshoot was used as the experimental criteria to compare the functionality between the autostop and clinically used needles. FIG. 33 shows the experimental set up. A cow eye sclera is placed in between two supports with opposite holes in the center. The holes are shaped in a manner that allows comfortable injection and appropriate recording from a video camera. The camera is set such it is possible to directly read the overshoot of the needle on a scale put close to the sample. Injections were performed by both trained and untrained users using same needle gauge (32 G) and length (½"). Results indicated that overshoot generated by the autostop needle is four time less important than the one generated by a regular syringe. The autostop needle overshoot 3300 was much less significant than that of the standard syringe overshoot 3302.

Example 8. Force Requirements for an Autostop Needle in a Sclera

Figures 34A, 34B:
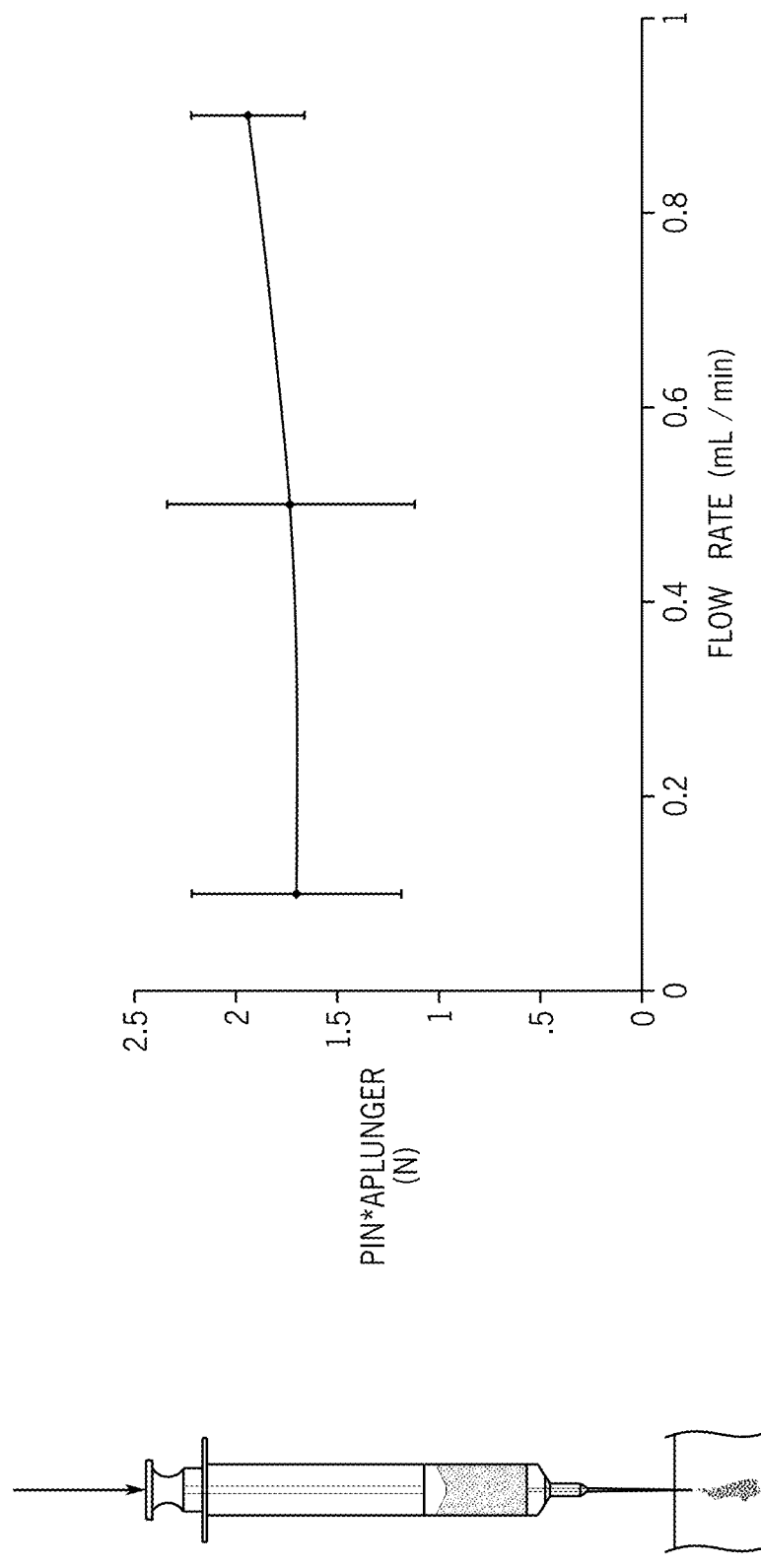
FIG. 34A shows a typical needle injection.
FIG. 34B shows the relationship between the force required to inject into specific tissue and the flow rate of the injection in accordance with the present disclosure.

FIGS. 34A and 34B show the technique and results of determining the force required to inject a liquid into the sclera, as opposed to the suprachoroidal cavity.

Example 9. Cutting and Shear Forces for an Autostop Needle in a Sclera

Figures 35A, 35B:
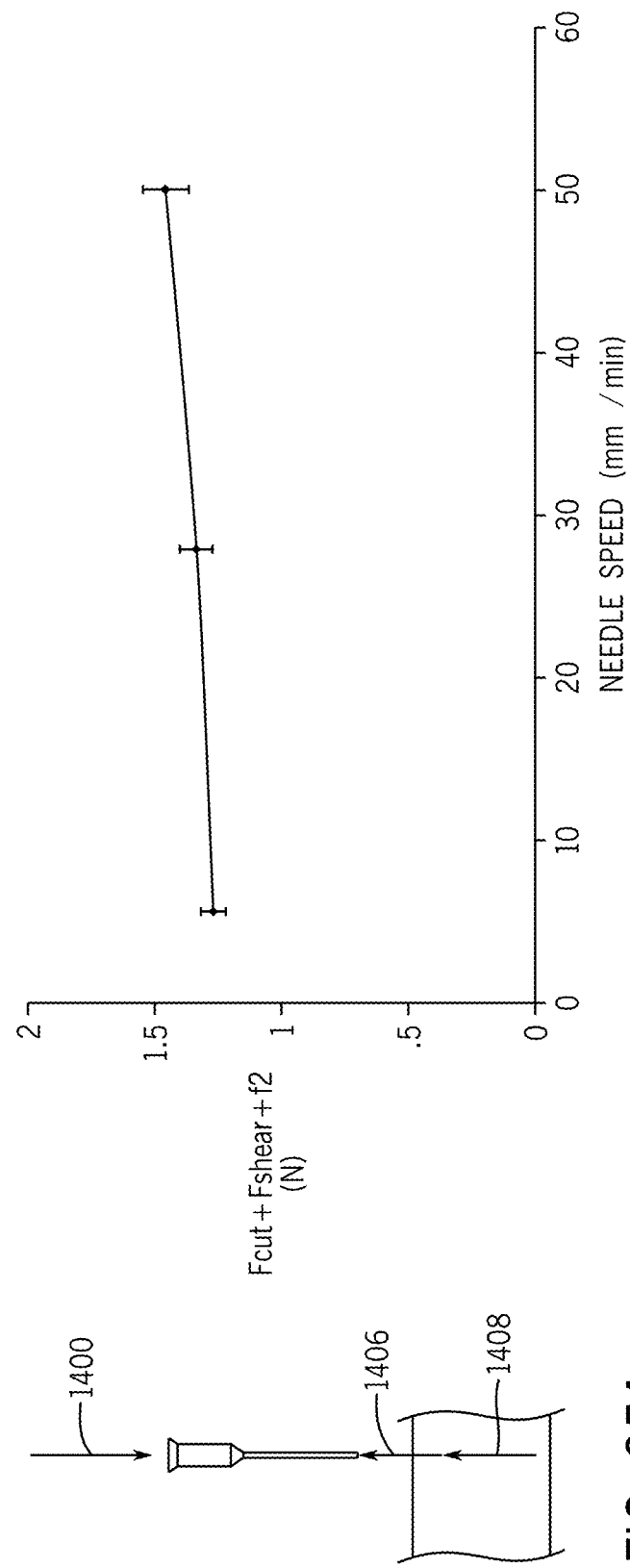
FIG. 35A shows a typical needle injection and the associated forces in accordance with the present disclosure.
FIG. 35B shows the relationship between the force required to puncture tissue and penetration relative to needle speed in accordance with the present disclosure.

FIGS. 35A and 35B show the technique and results of the sclera cutting force and sclera shear force when using a 33 G needle.

Example 10. Tissue Specifications Drive the Needle Penetration

Figure 36:
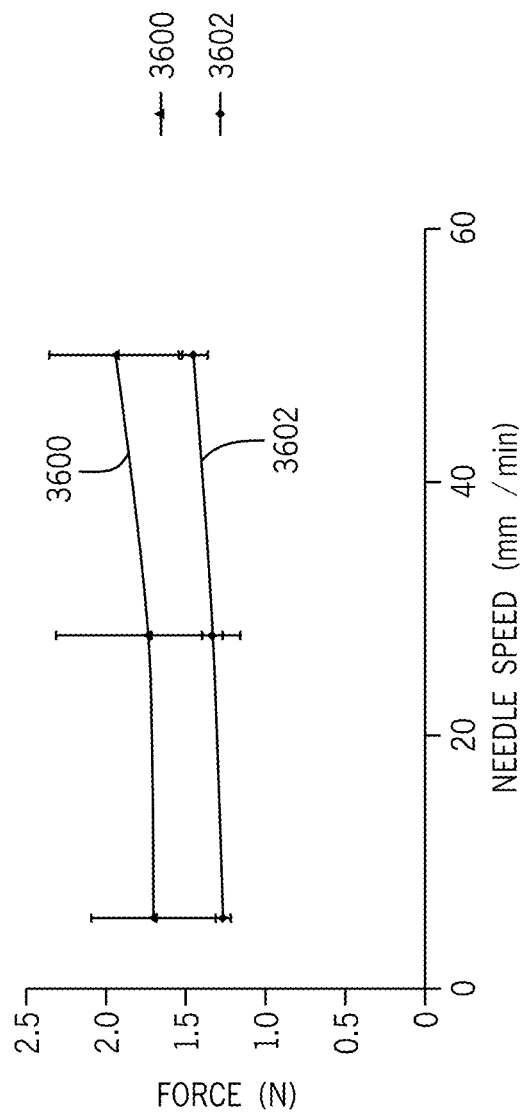
FIG. 36 shows the relationship between tissue specifications and needle penetration in accordance with the present disclosure.

FIG. 36 shows the injection force 3600 when compared to the combined forces 3602. This demonstrates that the injection force 3600 is greater than the combined forces 3602 of the provided tissue.

Beyond the specific examples provided above, other applications include accessing suprachoroidal space (ocular), performing epidural injections (spinal cord access), accessing large vessels (arteries/veins) for inserting surgical wires (e.g., to access heart through vessels), accessing vessels for fistula access or catheter insertion, inserting through heart wall without damaging inner wall, accessing the abdomen (e.g. trocar access for minimally invasive surgery), injecting in fat under the skin, accessing insides of amniotic sac without damaging the fetus, performing a knee sac injection without damaging cartilage, injecting inside meninges without damaging brain tissue (drill in skull then use autostop on meninges), injecting between pericardium and heart, injecting between fascia and kidney, injecting between fibrous tissue layer and implants (for e.g. breast implant), injecting into other ocular spaces (e.g., for Deep Anterior Lamellar Keratoplasty (DALK) to separate epithelial cell layer from collagenous layer), or accessing collapsed lungs from outside. Also, the system may be used to deliver gene therapy including but not limited to viral vectors and/or transfected cells. Similarly, a delivered fluid or substance may include a variety of therapeutics. As non-limiting examples, therapeutics may include mRNA, CRISPR agents, RNAi, antibodies, nanobodies, nanoparticles, proteins, peptides, small molecules, aptamers, cells, extracellular vesicles, microRNA and the like.

For the avoidance of doubt, aspects of the present disclosure described with respect to the systems are applicable to the methods and aspects described with respect to the methods are applicable to the systems.

It will be appreciated by those skilled in the art that while the present disclosure has been described above in connection with particular embodiments/aspects and examples, the disclosure is not necessarily so limited, and that numerous other aspects, examples, uses, modifications and departures from the aspects, examples and uses are intended to be encompassed by the claims attached hereto.

The invention claimed is:

1. A system for delivering an injection of a fluid into a void within a subject, the system comprising: a syringe barrel extending from a first end to a second end and forming a lumen extending from the first end to the second end; a plug arranged within the lumen proximate to the first end and forming a seal between the plug and the syringe barrel against the fluid movement from the lumen between the plug and the syringe barrel; a floating seal arranged within the lumen proximate to the second end forming a seal between the floating seal and the syringe barrel against the fluid movement from the lumen between the floating seal and the syringe barrel; a hollow needle extending from a proximal end connected to the floating seal to a distal end having an opening for the fluid to flow from the lumen, through the floating seal, and through the second end of the syringe barrel via the hollow needle; and wherein the syringe barrel, the plug, and the floating seal include material and dimensions selected based on a threshold flowrate for the fluid arranged within the lumen to: upon a force being applied to the fluid, overcome an opposing force to move the floating seal and the hollow needle from the second end of the syringe barrel and extend the distal end of the hollow needle into a tissue of the subject, and upon the distal end of the hollow needle extending beyond the tissue of the subject and into the void of the subject, succumb to the opposing force to displace the fluid into the void through the opening formed at the distal end of the hollow needle.

2. The system of claim 1 wherein, when overcoming the opposing force, the threshold flowrate for the fluid is not overcome, such that the fluid is not displaced through the opening in the distal end of the hollow needle until the opening in the distal end of the hollow needle passes from the tissue into the void.

3. The system of claim 1 wherein the void is pressurized, empty, fluid filled, porous, or potential space created by delamination of layers.

4. The system of claim 1 wherein the fluid is a first fluid, the system further comprising a drainage of a second fluid.

5. The system of claim 1 wherein the syringe barrel forms a single-handed injector.

6. The system of claim 1 wherein the syringe barrel is formed of two barrels coupled together by a lock connector, a flexible tube, or a rigid tube.

7. The system of claim 1 further comprising a back support extending into the lumen of the syringe barrel to restrict the floating seal from extending through the lumen toward the first end of the syringe barrel beyond the back support.

8. The system of claim 1 further comprising at least one of:
 a fluid connection extending through the plug to deliver the force via the fluid connection;
 a plunger arm extending from the plug to apply the force through the plunger arm; and
 a mechanical actuator configured to deliver the force by releasing potential energy stored in the mechanical actuator.

9. The system of claim 1 wherein the hollow needle is configured to extend beyond the second end of the syringe barrel to expose a portion of the hollow needle including into the opening for insertion into the tissue of the subject before applying the force.

10. The system of claim 1 wherein the hollow needle extends through the floating seal or is aligned with a passage extending through the floating seal to present a fluid passage from the lumen in the syringe barrel to the opening in the hollow needle.

11. The system of claim 1 wherein the hollow needle includes threads forming a drill or a sharpened tip forming a knife point.

12. The system of claim 1 wherein the fluid includes a liquid, a gas, a combination of liquid and gas, liquid-suspended particles, gel, gel-suspended particles, micro-particles, or nano-particles.

13. The system of claim 1 wherein a portion of the lumen between the plug and the floating seal forms a volume of one of 1 ml, 3 ml, 5 ml, or 10 ml prior to the displacement of the fluid.

14. The system of claim 1 wherein the opposing force includes at least one of a frictional force between the floating seal and the syringe barrel, a frictional force of the tissue of the subject or a spring based mechanical force.

15. The system of claim 14 wherein the threshold flowrate includes a minimum flowrate sufficient to enable the hollow needle to move in the void.

16. A method of delivering a fluid into a void within a subject that is formed within a tissue in the subject or between tissues in the subject, the method comprising: providing a syringe system including: a syringe barrel extending from a first end to a second end and forming a lumen extending from the first end to the second end; a plug arranged within the lumen proximate to the first end and forming a seal between the plug and the syringe barrel against the fluid movement from the lumen between the plug and the syringe barrel; a floating seal arranged within the lumen proximate to the second end forming a seal between the floating seal and the syringe barrel against the fluid movement from the lumen between the floating seal and the syringe barrel; a hollow needle extending from a proximal end connected to the floating seal to a distal end having an opening for the fluid to flow from the lumen, through the floating seal, and through the second end of the syringe barrel via the hollow needle;
  arranging the distal end of the hollow needle to extend into the tissue without applying a force to the fluid;
  applying a force to the fluid so that an opposing force is overcome to move the floating seal and the hollow needle from the second end of the syringe barrel and extend the distal end of the hollow needle further into the tissue of the subject; and
  continuing said applying the force to the fluid as the distal end of the hollow needle extends beyond the tissue of the subject and into the void as the floating seal succumbs to the opposing force to displace the fluid into the void through the opening formed at the distal end of the hollow needle.

17. The method of claim 16 wherein the void is formed by a suprachoroidal space between a sclera and a choroid of an eye of the subject.

18. The method of claim 16 wherein the fluid includes a therapeutic for a posterior segment eye disease.

19. The method of claim 18 wherein the posterior segment eye disease includes one of macular degeneration (AMD), diabetic retinopathy (DR), diabetic macular edema (DME), retinal vein occlusion (RVO), uveitis, or endophthalmitis.

20. A system for delivering an injection of a fluid into a void within a subject, the system comprising: a barrel extending from a first end to a second end and forming a lumen extending from the first end to the second end; a plug arranged within the lumen proximate to the first end and forming a seal between the plug and the barrel against the fluid movement from the lumen between the plug and the barrel; a floating seal arranged within the lumen proximate to the second end forming, a seal between the floating seal and the barrel against the fluid movement from the lumen between the floating seal and the barrel; a penetrating device including a passage extending from a proximal end connected to the floating seal to a distal end having an opening for the fluid to flow from the lumen, through the floating seal, and through the second end of the barrel via the penetrating device; and wherein the barrel, the plug, and the floating seal include material and dimensions selected based on a threshold flowrate for the fluid arranged within the lumen to: upon a force being applied to the fluid, overcome an opposing force to move the floating seal and the penetrating device from the second end of the barrel and extend the distal end of the penetrating device into a tissue of the subject, and upon the distal end of the penetrating device extending beyond the tissue of the subject and into the void of the subject, succumb to the opposing force to displace the fluid into the void through the passage and the opening formed at the distal end of the penetrating device.

* * * * *

UNITED STATES PATENT AND TRADEMARK OFFICE
CERTIFICATE OF CORRECTION

PATENT NO. : 11,413,397 B2
APPLICATION NO. : 16/469567
DATED : August 16, 2022
INVENTOR(S) : Jeffrey Karp et al.

It is certified that error appears in the above-identified patent and that said Letters Patent is hereby corrected as shown below:

In the Specification

Column 9, Line 22, "(Pin)" should read --($P_{in}$)--.

Signed and Sealed this
Fifteenth Day of November, 2022

*Katherine Kelly Vidal*

Katherine Kelly Vidal
*Director of the United States Patent and Trademark Office*